(12) United States Patent
Aneja et al.

(10) Patent No.: US 12,740,691 B2
(45) **Date of Patent: *Sep. 22, 2026**

(54) DEVICES, SYSTEMS, AND METHODS FOR PROVIDING SEALABLE ACCESS TO A WORKING CHANNEL

(71) Applicant: BOSTON SCIENTIFIC MEDICAL DEVICE LIMITED, Galway (IE)

(72) Inventors: Harchetan Singh Aneja, Amritsar (IN); Amit Bharos, Jabalpur (IN); Swami Upadhyay, Raipur (IN); Boopathi Rajarathnam, Salem (IN); Shalin Singh Rawat, Rishikesh (IN); Venkatesh Neelamegam, Tirupur (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 50 days.

This patent is subject to a terminal disclaimer.

(21) Appl. No.: 18/776,937

(22) Filed: Jul. 18, 2024

(65) Prior Publication Data

US 2024/0366068 A1 Nov. 7, 2024

Related U.S. Application Data

(63) Continuation of application No. 16/671,833, filed on Nov. 1, 2019, now Pat. No. 12,070,187.

(Continued)

(51) Int. Cl.

| | |
|---|---|
| ***A61B 1/00*** | (2006.01) |
| ***A61B 1/015*** | (2006.01) |

(Continued)

(52) U.S. Cl.

CPC ...... *A61B 1/00137* (2013.01); *A61B 1/00064* (2013.01); *A61B 1/0011* (2013.01);

(Continued)

(58) Field of Classification Search

CPC ............ A61B 1/00137; A61B 1/00064; A61B 1/0011; A61B 1/0014; A61B 1/00147; A61B 1/015; A61B 1/018; B29D 99/0053

See application file for complete search history.

(56) References Cited

U.S. PATENT DOCUMENTS

| | | | |
|---|---|---|---|
| 4,198,959 | A | 4/1980 | Otani |
| 4,649,904 | A | 3/1987 | Krauter et al. |

(Continued)

FOREIGN PATENT DOCUMENTS

| | | | |
|---|---|---|---|
| AU | 1999027921 | A | 12/1999 |
| AU | 2001056987 | A | 11/2001 |

(Continued)

OTHER PUBLICATIONS

Cook Medical—"Fusion® Wire guide Locking Device," 2 pages, Dec. 2017.

(Continued)

*Primary Examiner* — Timothy J Neal

(74) *Attorney, Agent, or Firm* — Seager Tufte Wickhem LLP

(57) ABSTRACT

The present disclosure relates generally to the field of medical devices such as endoscopes, endoscope assemblies, guide tubes, introducers, and instrument caps for endoscopes, guide tubes, and introducers. In particular, the present disclosure relates to biopsy cap configurations providing scalable access for medical instruments to a working channel, such as a working channel for an endoscope.

20 Claims, 29 Drawing Sheets

Related U.S. Application Data

(60) Provisional application No. 62/834,192, filed on Apr. 15, 2019, provisional application No. 62/834,201, filed on Apr. 15, 2019, provisional application No. 62/768,808, filed on Nov. 16, 2018, provisional application No. 62/755,024, filed on Nov. 2, 2018.

(51) Int. Cl.

| | |
|---|---|
| ***A61B 1/018*** | (2006.01) |
| ***A61B 10/02*** | (2006.01) |
| ***A61B 10/04*** | (2006.01) |
| ***B29D 99/00*** | (2010.01) |

(52) U.S. Cl.

CPC ........ *A61B 1/0014* (2013.01); *A61B 1/00147* (2013.01); *A61B 1/015* (2013.01); *A61B 1/018* (2013.01); *A61B 10/0275* (2013.01); *A61B 10/04* (2013.01); *B29D 99/0053* (2013.01)

(56) References Cited

U.S. PATENT DOCUMENTS

| | | | |
|---|---|---|---|
| 5,104,379 | A | 4/1992 | Nakamura et al. |
| 5,312,363 | A | 5/1994 | Ryan et al. |
| 5,743,884 | A | 4/1998 | Hasson et al. |
| 6,200,262 | B1 | 3/2001 | Ouchi |
| 6,595,946 | B1 | 7/2003 | Pasqualucci |
| 6,605,075 | B1 | 8/2003 | Burdulis |
| 6,663,598 | B1 | 12/2003 | Carrillo et al. |
| 6,863,661 | B2 | 3/2005 | Carillo, Jr. et al. |
| 6,893,393 | B2 | 5/2005 | Carrillo |
| 7,060,052 | B2 | 6/2006 | Windheuser et al. |
| 7,226,411 | B2 | 6/2007 | Akiba |
| 7,473,221 | B2 | 1/2009 | Ewers et al. |
| 7,637,863 | B2 | 12/2009 | Deal et al. |
| 7,670,285 | B2 | 3/2010 | Yamaya |
| 7,670,316 | B2 | 3/2010 | Windheuser et al. |
| 7,803,107 | B2 | 9/2010 | Carrillo |
| 7,967,744 | B2 | 6/2011 | Kaye et al. |
| 8,012,129 | B2 | 9/2011 | Bettuchi et al. |
| 8,152,774 | B2 | 4/2012 | Pasqualucci |
| 8,231,525 | B2 | 7/2012 | Cohen et al. |
| 8,333,693 | B2 | 12/2012 | Hamazaki |
| 8,343,041 | B2 | 1/2013 | Byers et al. |
| 8,388,521 | B2 | 3/2013 | Byers et al. |
| 8,480,570 | B2 | 7/2013 | Tinkham et al. |
| 8,647,256 | B2 | 2/2014 | Carrillo, Jr. |
| 8,702,596 | B2 | 4/2014 | Kaye et al. |
| 9,131,831 | B2 | 9/2015 | Byers et al. |
| 9,149,173 | B2 | 10/2015 | Scopton et al. |
| 9,566,145 | B2 | 2/2017 | Trainor et al. |
| 9,622,776 | B2 | 4/2017 | Oberlaender et al. |
| 9,955,998 | B2 | 5/2018 | Kleyman |
| 9,986,895 | B2 | 6/2018 | Meloul |
| 11,064,870 | B2 | 7/2021 | Rajarathnam et al. |
| 12,070,187 | B2 * | 8/2024 | Aneja ................ A61B 1/00064 |
| 2005/0171402 | A1 | 8/2005 | Cohen et al. |
| 2006/0195117 | A1 | 8/2006 | Rucker et al. |
| 2007/0238928 | A1 | 10/2007 | Maseda et al. |
| 2007/0244356 | A1 | 10/2007 | Carrillo et al. |
| 2007/0282166 | A1 | 12/2007 | Ayala et al. |
| 2007/0293719 | A1 | 12/2007 | Scopton et al. |
| 2008/0290605 | A1 | 11/2008 | Brockmeier et al. |
| 2009/0005799 | A1 | 1/2009 | Franer et al. |
| 2009/0088600 | A1 | 4/2009 | Meloul |
| 2009/0287052 | A1 | 11/2009 | Amos et al. |
| 2010/0081878 | A1 | 4/2010 | Byers et al. |
| 2010/0087705 | A1 | 4/2010 | Byers et al. |
| 2010/0087710 | A1 * | 4/2010 | Weldon ................. A61B 1/018 600/123 |
| 2010/0240956 | A1 | 9/2010 | Secrest et al. |
| 2012/0004507 | A1 | 1/2012 | Kaye |
| 2012/0071713 | A1 | 3/2012 | Kaye et al. |
| 2012/0253128 | A1 | 10/2012 | Yamane |
| 2013/0150793 | A1 | 6/2013 | Beissel et al. |
| 2013/0304116 | A1 * | 11/2013 | Yamane ............ A61B 1/00137 606/205 |
| 2014/0187866 | A1 | 7/2014 | Kaye et al. |
| 2015/0190170 | A1 | 7/2015 | Frederick et al. |
| 2016/0206859 | A1 | 7/2016 | Eden |
| 2017/0202438 | A1 | 7/2017 | Ogi |
| 2017/0319828 | A1 | 11/2017 | Doepker et al. |
| 2018/0310806 | A1 | 11/2018 | Gavalis et al. |
| 2019/0046016 | A1 | 2/2019 | Rajarathnam et al. |
| 2020/0138272 | A1 | 5/2020 | Neelamegam et al. |
| 2020/0138273 | A1 | 5/2020 | Neelamegam et al. |
| 2020/0138274 | A1 | 5/2020 | Aneja et al. |
| 2020/0138276 | A1 | 5/2020 | Aneja et al. |
| 2020/0138277 | A1 | 5/2020 | Aneja et al. |
| 2020/0138419 | A1 | 5/2020 | Aneja et al. |

FOREIGN PATENT DOCUMENTS

| | | | |
|---|---|---|---|
| CN | 105816208 | A | 8/2016 |
| CN | 205697867 | | 11/2016 |
| EP | 1406691 | | 4/2004 |
| EP | 1997444 | | 12/2008 |
| EP | 2505119 | | 10/2012 |
| EP | 2325340 | | 11/2012 |
| EP | 2564758 | | 3/2013 |
| EP | 2574271 | | 11/2014 |
| EP | 2020901 | | 7/2016 |
| JP | S6129703 | U | 2/1986 |
| JP | H1057302 | A | 3/1998 |
| JP | H11253396 | A | 9/1999 |
| JP | 2001104315 | | 4/2001 |
| JP | 2003533297 | A | 11/2003 |
| JP | 2005080867 | | 3/2005 |
| JP | 2008123063 | | 5/2008 |
| JP | 2008148734 | A | 7/2008 |
| JP | 2009268777 | A | 11/2009 |
| WO | 0187398 | A2 | 11/2001 |
| WO | 2005011791 | A2 | 2/2005 |
| WO | 2007117750 | A2 | 10/2007 |
| WO | 2008101286 | A1 | 8/2008 |
| WO | 2009143129 | A1 | 11/2009 |
| WO | 2009143137 | A1 | 11/2009 |
| WO | 2018024109 | A1 | 2/2018 |
| WO | 2019033006 | A1 | 2/2019 |

OTHER PUBLICATIONS

Cook Medical—"Fusion® Wire Guide Locking Device," URL: https://www.cookmedical.com/products/esc fswl webds/@Cook 4 pages, 2021.

International Search Report and Written Opinion for International Application No. PCT/IB2019/059407, mailed on Feb. 14, 2020 (11 pages).

International Search Report and Written Opinion for International Application No. PCT/IB2019/059408, mailed on Feb. 14, 2020 (12 pages).

International Search Report and Written Opinion for International Application No. PCT/IB2019/059409, mailed on Feb. 13, 2020 (11 pages).

International Search Report and Written Opinion for International Application No. PCT/IB2019/059413, mailed on Feb. 17, 2020. (10 pages).

International Search Report and Written Opinion for International Application No. PCT/IB2019/059411, mailed on Jun. 25, 2020. (14 pages).

Invitation to Pay Additional Fees and, Where Applicable, Protest Fee forInternational Application No. PCT/IB2019/059411, mailed on Feb. 14, 2020. (9 pages).

International Search Report and Written Opinion for International Application No. PCT/IB2019/059404, mailed on Feb. 17, 2020. (10 pages).

* cited by examiner

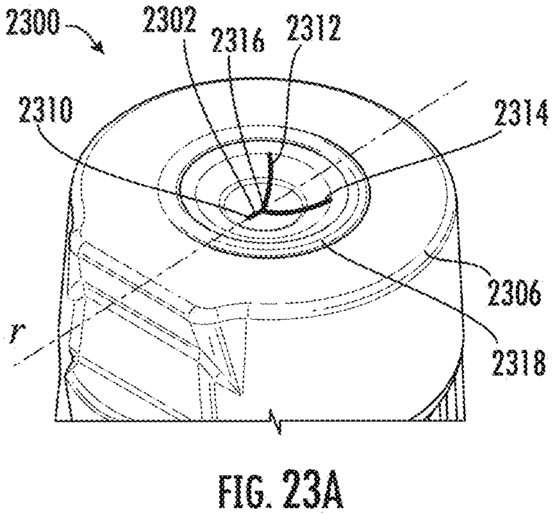
FIG. 23A
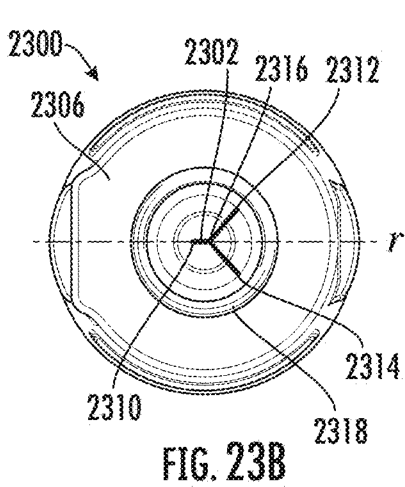
FIG. 23B
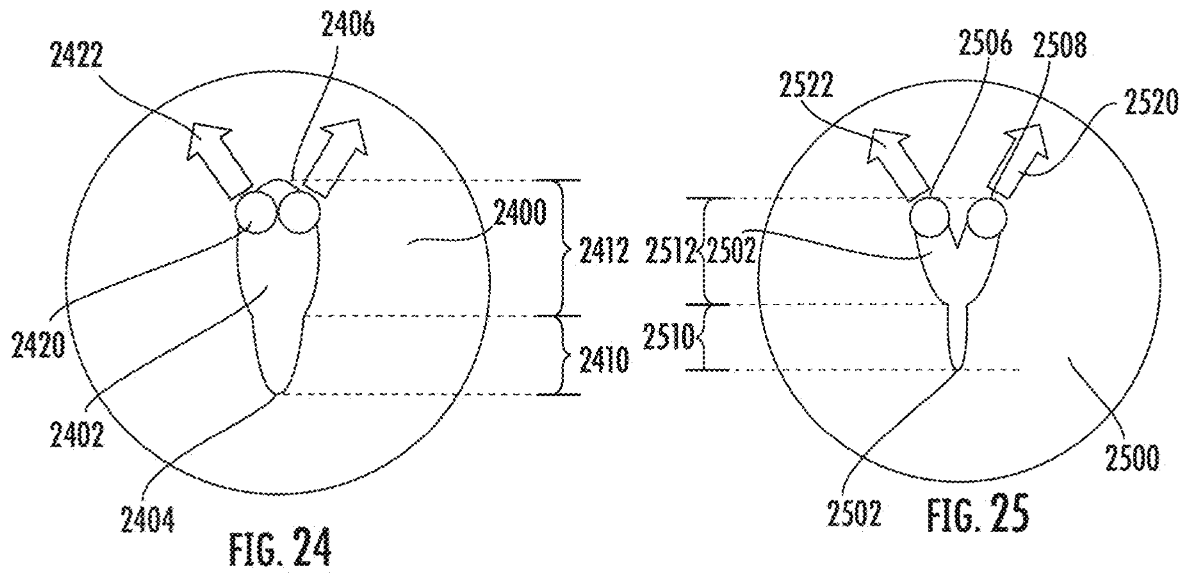
FIG. 24
FIG. 25

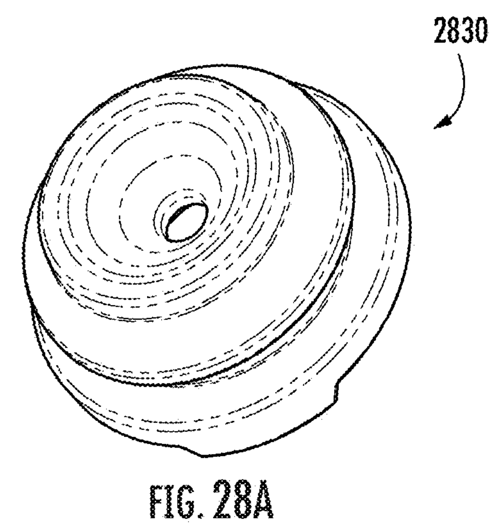
FIG. 28A
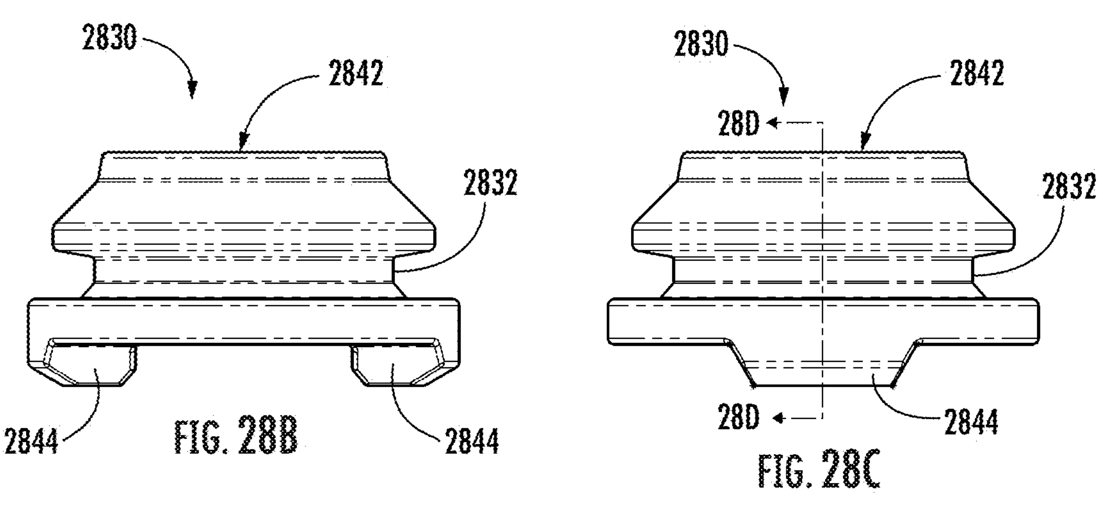
FIG. 28B
FIG. 28C
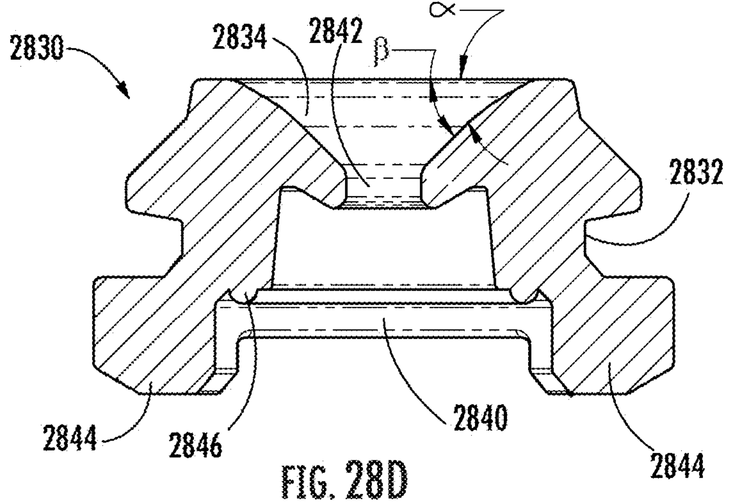
FIG. 28D

DEVICES, SYSTEMS, AND METHODS FOR PROVIDING SEALABLE ACCESS TO A WORKING CHANNEL

PRIORITY

This application is a continuation of and claims the benefit of the earlier filing date of U.S. patent application Ser. No. 16/671,833, filed Nov. 1, 2019, which claims the benefit of priority under 35 USC § 119 to U.S. Provisional Patent Application No. 62/755,024, filed Nov. 2, 2018, and U.S. Provisional Patent Application No. 62/768,808, filed Nov. 16, 2018, and U.S. Provisional Patent Application No. 62/834,192, filed Apr. 15, 2019, and to U.S. Provisional Patent Application Ser. No. 62/834,201, filed Apr. 15, 2019, which applications are incorporated herein by reference in their entireties for all purposes. Any and all priority claims identified in the Application Data Sheet, or any correction thereto, are hereby incorporated by reference under 37 C.F.R. § 1.57.

FIELD

The present disclosure relates generally to the field of medical devices such as endoscopes, endoscope assemblies, guidewires, guide tubes, introducers, and instrument caps for endoscopes, guidewires, guide tubes, and introducers. In particular, the present disclosure relates to biopsy cap configurations providing sealable access for medical instruments to a working channel, such as a working channel for an endoscope.

BACKGROUND

In endoscopic procedures, for example, medical professionals are faced with the challenge of accessing patient anatomy with medical instruments through a working channel of an endoscope while preventing undesired fluid exchange through the inlet or proximal port of the working channel and between the patient and the atmosphere. For example, bile, air, or other fluids may undesirably enter or escape the patient. Poor leakage prevention may cause unhygienic environments for the medical professional or the patient, increasing the chances of health concerns such as infection and increasing the medical professional's frustration during a procedure.

It is with these considerations in mind that a variety of advantageous medical outcomes may be realized by the medical devices, systems, and methods of the present disclosure.

SUMMARY

Embodiments of the present disclosure may assist generally with biopsy cap configurations providing sealable access for medical instruments to a working channel of medical device, such as a working channel for an endoscope, including design, material, manufacturing method, and use alternatives for such medical devices.

In an embodiment, a seal assembly may include a biopsy cap having an inner chamber therein, a cap aperture at a first end in fluid communication with the inner chamber, and a securing member at a second end. A plurality of seal members may be disposed within the inner chamber, each seal member having a seal aperture in fluid communication with the cap aperture. A base may be disposed within the securing member, the base having a base aperture therethrough in fluid communication with each of the seal apertures.

In various embodiments described here or otherwise, the base may include a recess configured to engage the securing member. The recess may be an external annular recess. A proximal end of the base may have a slope towards the base aperture, the slope having a first angle that transitions to a second angle, wherein the second angle is between the first angle and the aperture, and wherein the second angle is larger than the first angle. The first angle may be about 30° and the second angle may be about 45°. The base may include at least two extensions that extend distally from the base and are configured to engage a port of a working channel. Each of the apertures of the plurality of seal members may be axially aligned with each other, the base aperture, and the cap aperture. At least one of the plurality of seal members may include a plurality of surfaces extending radially about the seal aperture in a helical pattern. At least one of the plurality of seal members may include a plurality of projections extending radially inward towards the seal aperture, wherein the plurality of projections are angularly offset layers. The plurality of projections may define the seal aperture at the center of the seal member such that the seal aperture extends axially through the seal.

In an embodiment, a device may be configured to attach to a port of an endoscope. An aperture may be through the device in fluid communication with the port. At least two extensions may extend distally from the base and are configured to engage a port of a working channel. A recess may be disposed about the device configured to engage a biopsy cap.

In various embodiments described here or otherwise, the recess may be an external annular recess. A proximal end of the base may have a slope towards the aperture, the slope having a first angle that transitions to a second angle, wherein the second angle is between the first angle and the aperture, and wherein the second angle is larger than the first angle. The first angle may be about 30° and the second angle may be about 45°. The base may include at least two extensions that extend distally from the base and are configured to engage a port of a working channel. A ridge may be about the aperture configured to compressively seal against the port.

In an embodiment, a seal system may include an endoscope having a working channel and a port at a proximal end of the working channel. A base may be disposed about the port, the base having a base aperture therethrough. A biopsy cap having a cap aperture therethrough, and a securing member may be at an end of the biopsy cap, the securing member disposed about the base such that the cap aperture is in fluid communication with the base aperture and the port.

In various embodiments described here or otherwise, a medical instrument may extend through the cap aperture, the base aperture, and the port. The base may include at least two extensions that extend distally from the base and are configured to engage the port of the working channel. A seal member may be disposed within an inner chamber of the biopsy cap, the seal member having a seal aperture in fluid communication with the cap aperture.

In an embodiment, a medical device may include a seal for use in combination with an endoscope. The seal may comprise a main body including a circumferential outer wall surrounding a central lumen. The main body may have a top surface and a bottom surface, and a plurality of projections extending radially inward from the outer wall towards a center of the lumen. The plurality of projections may be arranged in a series of circumferentially and angularly offset layers, wherein each layer includes a plurality of projections.

In various embodiments, the plurality of projections may define an opening at the center of the lumen, the opening extending axially through the seal. The series of angularly offset layers may extend axially along the main body such that the projections spiral downward around the seal from the top surface to the bottom surface of the main body. Each layer may include the same number of projections. The plurality of projections in each layer may be circumferentially spaced apart. Each layer may include between three and fifteen projections. The plurality of projections may be arranged in between three and fifteen layers. Each layer of projections may be offset by between ten and forty degrees from adjacent layers. An outer surface of the outer wall may include a plurality of axial slits.

In an embodiment, a method of making a seal for use in combination with an endoscope may include molding a seal as a single piece element. The seal may be molded to have a main body including a circumferential wall surrounding a central lumen, and a plurality of projections extending radially outward from the wall away from the lumen. The plurality of projections may be molded in a series of circumferentially and angularly offset layers, The molded seal may be turned inside out such that the plurality of projections extend radially inward toward a center of the central lumen.

In various embodiments, molding the seal may include assembling a multi-piece radially ejectable mold around a core element. The core element may define the shape of the wall and the multi-piece mold defines the shape and orientation of the plurality of projections. Molding may include injection molding the seal and then disassembling the multi-piece mold. Molding the seal may include assembling an axial staked mold including a top and a base and a plurality of plates. Each plate may define the shape and orientation of one layer of projections. Molding may include injection molding the seal and then disassembling the axial staked mold.

In an embodiment, a seal for use in combination with an endoscope may include a main body including a circumferential outer wall surrounding a central lumen. The main body may have a top surface and a bottom surface, at least one support wall extending radially from the outer wall towards a center of the lumen, and at least one helical flap extending from the support wall helically downward along an inner surface of the outer wall. At least one helical flap may define an opening at the center of the lumen.

In various embodiments, the at least one helical flap may extend downward in a first direction helically along the inner surface of the outer wall and in a second direction radially towards the center of the lumen. The at least one support wall may consist of only first and second support walls and the at least one helical flap consists of only first and second helical flaps. The first helical flap may extend from a top surface of the first support wall to a bottom surface of a second support wall. Each helical flap may have a first end adjacent the top surface of the main body and a second end that extends below the bottom surface of the main body. The opening may be defined in part as a space between the first and second support walls, the space having a first diameter adjacent the top surfaces of the first and second support walls and a second diameter adjacent the bottom surfaces of the first and second support walls. The first and second support walls may be disposed directly opposite one another. The seal may be disposed within a cavity of a biopsy cap. The biopsy cap may have a base with a securing member for securing the biopsy cap to a port on the endoscope. The biopsy cap may have a locking member and an outer shell defining the cavity.

In an embodiment, a device for providing reinforced sealable access to a working channel may include a tubular body having a proximal end, a distal end and a longitudinal axis. The distal end of the tubular body may be configured to be removably disposed on a proximal end of the working channel in fluid communication therewith. A substantially linear aperture may be at the proximal end of the body configured to allow one or more medical instruments to be passed therethrough and, at the same time, substantially seal against fluids from the working channel passing therethrough. A plurality of reinforcing ribs may be arrayed about the aperture to reinforce the aperture against tearing.

In various embodiments described here and otherwise, the aperture may be substantially closed when there are no medical instruments passing therethrough. The ribs may extend radially in a plane substantially transverse to the longitudinal axis. Each rib of the plurality of ribs may have a width dimension in the transverse plane and a thickness dimension in a plane substantially parallel to the longitudinal axis. One or more of the ribs may extend substantially perpendicular to the aperture. Ribs extending substantially perpendicular to the aperture may have a greater width than the width of any other of the plurality of ribs. The ribs may have a greater width and thickness as they extend radially away from the aperture. The ribs may continuously increase in width and thickness as they extend radially away from the aperture. One or more of the ribs may have a greater thickness than the thickness of one or more of the other of the ribs. The tubular body may be hollow. The ribs may be disposed on a surface internal to the hollow tubular body. The ribs may be arranged symmetrically in a circular pattern around the aperture in the transverse plane. The tubular body may comprise silicone. The device may be a biopsy cap for sealable access to the working channel of an endoscope. A force required to tear the aperture of a body having ribs may be greater than the tear force for the aperture without the ribs.

In another embodiment, a device for providing reinforced sealable access to a working channel may include a tubular body having a proximal end, a distal end and a longitudinal axis. The distal end of the tubular body may be configured to be removably disposed on a proximal end of the working channel in fluid communication therewith. A substantially linear aperture at the proximal end of the body may be configured to allow one or more medical instruments to be passed therethrough and, at the same time, substantially seal against fluids from the working channel passing therethrough. A reinforcing ridge may extend about the aperture to reinforce the aperture against tearing.

In various embodiments described here and otherwise, the body may be hollow. The ridge may be disposed on a proximal surface of the body. The ridge may be spaced away from the aperture. The ridge may be resistant to tearing. The ridge may comprise a perimeter outline about the aperture that is ellipsoidal, circular, or oval. The ridge may have a cross section in a plane parallel to the longitudinal axis that comprises a substantially half moon shape. The aperture may be substantially closed when there are no medical instruments extending therethrough.

In yet another embodiment, a device for providing reinforced sealable access to a working channel may include a tubular body having a proximal end, a distal end and a longitudinal axis. The distal end of the tubular body may be configured to be removably disposed on a proximal end of the working channel in fluid communication therewith. An aperture may be at the proximal end of the body having a first and a second end. The aperture may be configured to allow one or more medical instruments to be passed therethrough and, at the same time, substantially seal against fluids from the working channel passing therethrough. The aperture may include a reinforced pattern that extends in a plane substantially transverse to the longitudinal axis in more than one dimension.

In various embodiments described here and otherwise, the aperture may include a third end. The aperture may extend substantially linearly from the first end to a split point. The aperture may extend substantially linearly from the split point to the second end. The aperture may extend substantially linearly from the split point to the third end. The aperture may extend from the split point to the second end at an angle degree from the split point to the first end. The aperture may extend from the split point to the third end at the same angle degree from the split point to the first end. A length of the aperture extending from the first end to the split point may be smaller than a length of the aperture extending from the split point to the second end. A length of the aperture extending from the split point to the third end may be substantially the same as the length of the aperture extending from the split point to the second end. The second and the third end may each be configured to accept and substantially fix a guidewire.

The above summary of embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 23A illustrates an isometric view of a biopsy cap including an aperture extending in more than one dimension, according to an embodiment of the present disclosure.

FIG. 23B illustrates a top view of the biopsy cap of FIG. 23A.

FIG. 24 illustrates a top view of a biopsy cap.

FIG. 25 illustrates a top view of a biopsy cap including an aperture extending in more than one dimension, according to an embodiment of the present disclosure.

FIG. 28A illustrates a perspective view of a base, according to an embodiment of the present disclosure.

FIG. 28B illustrates a side view of the base of FIG. 28A.

FIG. 28C illustrates a front view of the base of FIG. 28A.

FIG. 28D illustrates a cross-sectional view of the base of FIG. 28A.

Figure 1:
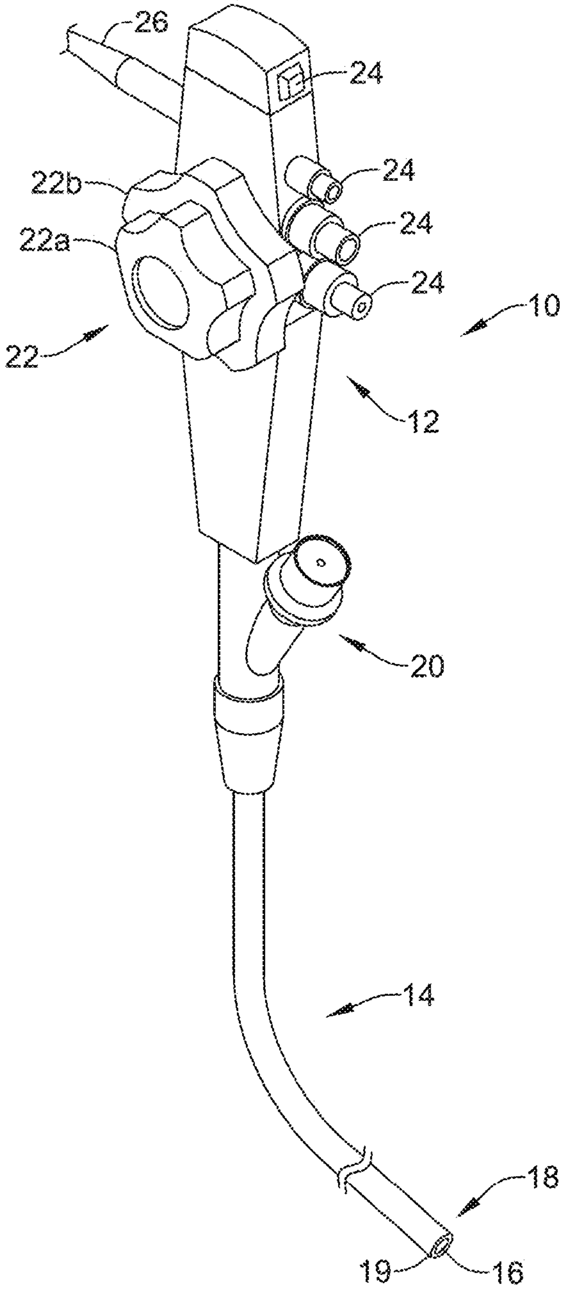
FIG. 1 is a perspective view of an example endoscope assembly with a biopsy cap, according to an embodiment of the present disclosure.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with reference to endoscopes, it should be appreciated that such devices, systems, and methods may be used with a variety of medical or other devices that include valves, working channels, ports, apertures, channels, and the like.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional along a medical device when introducing the device into a patient, while the term "proximal" refers to the end closest to the medical professional along the medical device when introducing the medical device into a patient.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the term "valve" may refer to an aperture, an opening, a slit, a slot, a seal, a seal member having multiple radial or axial protrusions, projections, or walls, either alone, in conjunction with, or integral with a biopsy cap or assembly.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

A wide variety of endoscope assemblies, biopsy caps, and seals have been developed. Of the known endoscope assemblies, biopsy caps, and seals, each has certain advantages and disadvantages. There is an ongoing need to provide alternative endoscope assemblies, biopsy caps, and seals as well as methods for making and using the same.

In an attempt to achieve controlled fluid exchanges, a biopsy cap in line with the working channel (e.g., attached to the inlet/proximal port of the working channel) of an endoscope may provide sealable instrument access to the working channel while restricting undesired fluids from entering or exiting. These functions may generally be inversely related, such that as it is made easier for the medical professional to pass instruments through the biopsy cap, it may be harder to prevent fluids from leaking through the biopsy cap. Conversely, a biopsy cap designed for significant leakage prevention may require additional force from a medical professional to pass medical instruments through the biopsy cap, which may be difficult for delicate instruments or for instruments having a large diameter. Additionally, as medical instruments are moved through the biopsy cap and/or locked into a position, the biopsy cap may be damaged, which may compromise leak prevention.

Endoscopic procedures, which may include installing a biopsy cap including a valve in-line with a working channel of an endoscope, are used as context for biopsy cap embodiments described herein, but it should be understood that these and other embodiments within the scope of the present disclosure may be applicable in other disciplines, products and procedures, as mentioned above. Endoscopic procedures may include, e.g., attaching a biopsy cap to an inlet or proximal port of the endoscope working channel. The endoscope may then be inserted into a body cavity or lumen of a patient. The body cavity or lumen may then be insufflated to improve visualization and to provide a working space therein. In doing so, a positive pressure may be created in the body and in the channel. The pressure may be retained by the installed biopsy cap. At least one aperture within the biopsy cap may be configured to open, grip, and seal around one or more medical instruments that are inserted through the biopsy cap. In addition to substantially preventing the exchange of fluids across the valve(s), seal member(s), and/or aperture(s) of the cap (i.e., into and out of the working channel and/or patient), the valve(s) may "squeegee" liquids from the outer surface of the instrument as it is inserted or withdrawn. The at least one aperture is configured to substantially or completely close when unoccupied by an instrument to prevent the exchange of fluids and/or insufflation loss.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified. An example endoscope and/or endoscope assembly 10 is illustrated in FIG. 1. Endoscope 10 may be any of a number of types of endoscopes or related medical devices usually identified by the particular anatomy desired to be reached. For example, endoscope 10 may be a bronchoscope, colonoscope, duodenoscope, esophagoscope, guide tubes, introducers (with or without vision or visualization capabilities), or any other type of endoscope or related medical device. Endoscope 10 may include a handpiece 12 and an elongate shaft 14 extending distally from handpiece 12 to a distal tip 18. Shaft 14 may include a lumen defining a working channel 16 extending through shaft 14 from a distal end 19 near distal tip 18 of shaft 14 to an access port 20 that may be positioned in handpiece 12 or another portion of endoscope 10. Although endoscope 10 is depicted with a single working channel in FIG. 1, it can be appreciated that in other embodiments, endoscope 10 may include multiple working channels, as desired.

Handpiece 12 may include one or a plurality of controls 22, such as rotating knobs, which may be used to control movement of distal tip 18 of shaft 14 during operation. For example, a first rotating knob **22*a* may control up and down movement or deflection of distal tip 18 of shaft 14, while a second rotating knob 22*b* may control side-to-side movement or deflection of distal tip 18 of shaft 14. Handpiece 12 may also include one or a plurality of buttons 24, which may be used to activate suction or deliver fluid such as air, saline and/or water, etc. through a lumen of the endoscope 10 or perform other functions as desired. Additionally, handpiece 12 may include an optical cable 26** connected to an external light source (not shown).

Figure 2:
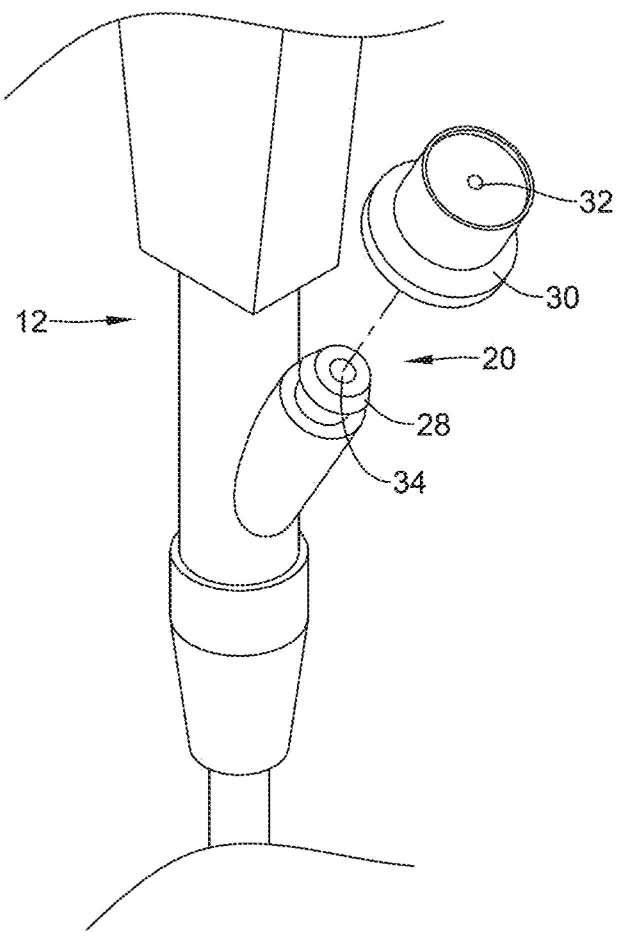
FIG. 2 is an exploded view of a portion of the example endoscope assembly shown in FIG. 1 illustrating the biopsy cap, according to an embodiment of the present disclosure.

With reference to FIG. 2, access port 20 of handpiece 12, which provides access to working channel 16 of endoscope 10, is illustrated. Access port 20, which may extend from the side of endoscope 10 or at another location, may include a coupling portion 28 for coupling a cap 30 to access port 20. Cap 30, which may be removably attached or permanently attached to access port 20, may provide access for inserting and/or advancing an endoscopic device through working channel 16 of endoscope 10.

Caps like cap 30, which may be termed "biopsy caps", are often designed with several functions in mind. For example, cap 30 may form a fluid/air barrier to working channel 16 that may help control insufflation and bile fluid egress therefrom that later have the potential to spill onto the clinician's hands and/or the floor thereby interfering with the intervention and/or become a biohazard. In addition, cap 30 may have an opening 32 extending therethrough. Opening 32 may be in fluid communication with working channel 16 and it may reduce the size of the opening 34 of working channel 16, for example, to accommodate an endoscopic device or instrument. Thus, caps like cap 30 may be much like an adapter in that it forms a physical transition at opening 34 of working channel 16 (or other instrument channels or access points) so that it transitions to a size more closely to that of the device to be inserted into working channel 16. Some additional discussion regarding biopsy caps can be found in U.S. Pat. Grant U.S. Pat. No. 9,149,173, filed Jun. 20, 2006 and titled "Medical Device For Use In Endoscopic Procedure," U.S. patent application Ser. No. 11/405,655, filed Apr. 17, 2006 and titled "Elongate Medical Devices Having An Improved Distal Profile For Use With An Endoscope," and to U.S. patent application Ser. No. 11/400,806, filed Apr. 7, 2006 and titled "Biopsy port for easy device passage," the disclosures of which are herein incorporated by reference in their entirety and for all purposes.

In various embodiments, features and advantages of providing sealable access to a working channel, e.g., of an endoscope, may be realized in combination with a biopsy cap and biopsy cap housing. Such sealable access to a working channel, which may be reinforced, may be implemented with features throughout the disclosures of U.S. patent application Ser. No. 16/100,960, filed Aug. 10, 2018 and titled "Biopsy Cap For Use With Endoscope," now U.S. Pat. No. 11,064,870, issued Jul. 20, 2021, U.S. patent application Ser. No. 16/671,879, filed on Nov. 1, 2019, and titled "Attachments For Endoscopes," now U.S. Pat. No. 12,256,895 issued Mar. 25, 2025, U.S. patent application Ser. No. 16/671,889, filed on Nov. 1, 2019, and titled "Biopsy Cap And Biopsy Cap Housing," now U.S. Pat. No. 11,690,499, issued Jul. 4, 2023, U.S. patent application Ser. No. 16/671,805, filed on Nov. 1, 2019, and titled "Devices, Systems, And Methods For A Biopsy Cap And Housing," now U.S. Pat. No. 12,245,746, issued Mar. 11, 2025, U.S. patent application Ser. No. 16/671,850, filed on Nov. 1, 2019, and titled "Internal Seal for Biopsy Cap," now U.S. Pat. No. 11,771,307, issued Oct. 3, 2023, U.S. patent application Ser. No. 16,671,786, filed on Nov. 1, 2019, and titled "Devices, Systems, and Methods for Providing Sealable Access to a Working Channel," now U.S. Pat. No. 11,478, 233, issued Oct. 25, 2022, which are each incorporated by reference in their entirety and for all purposes.

Although embodiments of the present disclosure are described with specific reference to biopsy caps and biopsy cap housings configured to allow the delivery and/or exchange of a variety of medical devices through the biopsy cap and port of an endoscope, laparoscope, or other visualization systems such as the Spy Glass™ Direct Visualization System (Boston Scientific Corp., Marlborough, MA), it should be appreciated that such designs may be adapted to fit and/or be used with a variety of medical devices and medical applications which include sealable access.

Additionally, a number of biopsy caps are contemplated that incorporate at least some of the desirable features of biopsy caps as well as have other desirable characteristics. The description discloses some of the embodiments of caps that are contemplated. These caps may include a passive seal. For the purposes of this disclosure, a passive seal is a seal that seals endoscope 10 at port 20 (e.g. of FIG. 1) so as to prevent the leakage of bodily fluids and/or air. In addition, by virtue of being "passive", the seals disclosed herein are configured to seal off endoscope 10 at port 20 without the need of any so-called "active" processes or steps by the clinician.

Figure 3:
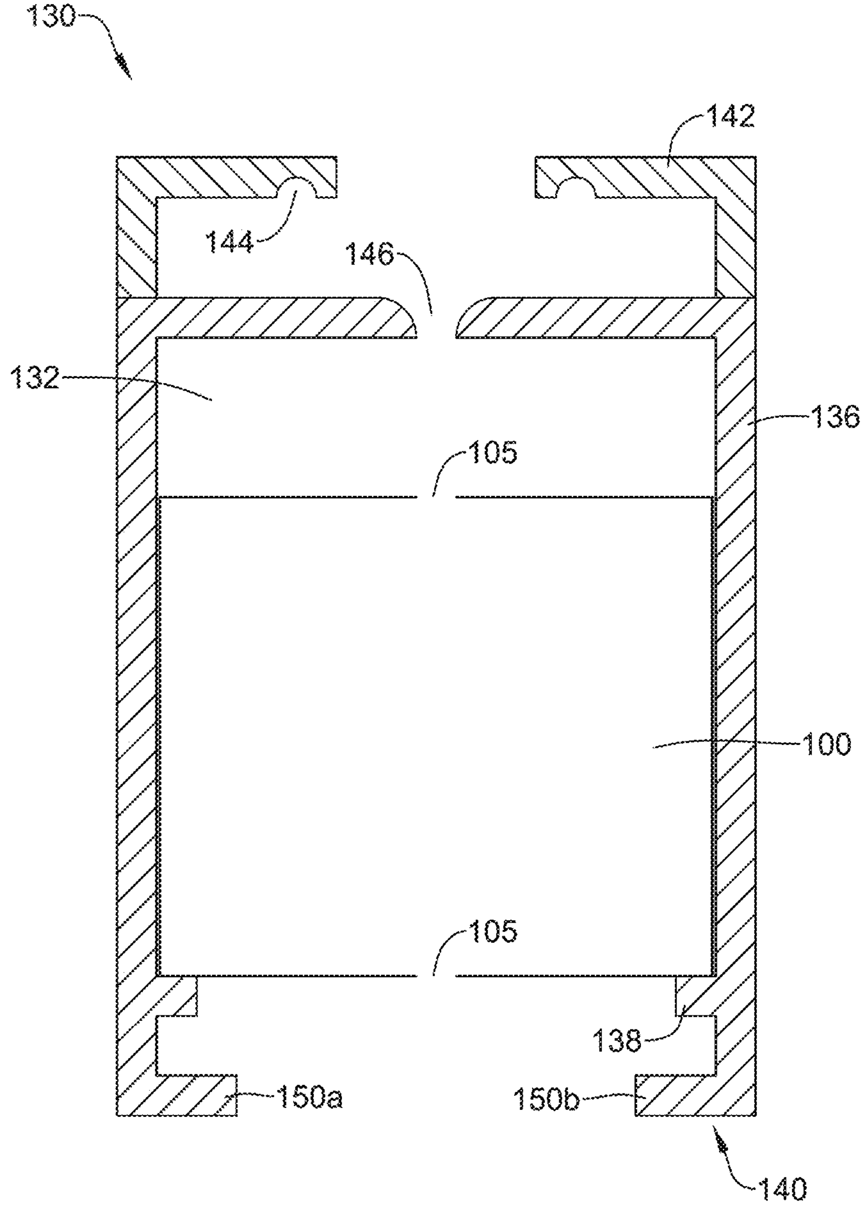
FIG. 3 is a cross-sectional view of a biopsy cap, according to an embodiment of the present disclosure.

With reference to FIG. 3, an embodiment of a biopsy cap 130 is illustrated according to the present disclosure. The biopsy cap 130 includes an outer shell 136 defining an inner chamber 132, a securing member 140 that may help to secure cap 130 to a port 20 (e.g. of FIG. 1), one or more locking members 142 coupled to the shell 136, and an inner seal member 100 disposed within outer shell 136. Outer shell 136 may take a number of different shapes and forms. In general, however, outer shell 136 may be made from a relatively rigid or hard polymer/plastic, a metal or metal alloy, a ceramic, and the like, or combinations thereof and may take a form resembling an exoskeleton or protective covering over the more delicate interior (e.g., seal member 100). In addition, by virtue of forming outer shell 136 from a relatively rigid material, a number of accessories to and/or structural components of cap 130 may be secured to or integrally formed with shell 136. For example, securing member 140 and/or locking members 142 may be secured to or integrally formed with outer shell 136.

An outer shell 136 may have one or more apertures 146 formed therein. Aperture 146, for example, may be disposed on a top surface or surface that is opposite securing member 140, although any other suitable portion of outer shell 136 may include aperture 146 including the sides or side surfaces. Aperture 146 may be the entrance point or otherwise define one or more openings that extend through the inner chamber 132 of the cap 130 and into working channel 16 (e.g., of FIG. 1) when cap 130 is seated on port 20. For example, aperture 146 may extend through outer shell 136 and provide access to the seal member 100. Thus, aperture 146 may form the exterior opening in cap 130 where other medical devices (e.g., guidewires, catheters, etc.) can be passed through so as to gain access to working channel 16 via seal member 100. Cap 130 may include a flange 138 extending into the inner chamber 132. The seal member 100 may sit on the flange 138. Seal member 100 may have openings 105 in top and bottom surfaces thereof which may be aligned longitudinally with the aperture 146 in the cap 130. Aperture 146 may guide the medical devices into the opening 105 and through the seal member 100.

In various embodiments, an aperture 146 may have a chamfered or beveled edge, which may function like a funnel to guide the medical device into the aperture 146 and may assist the ability of a user to pass a medical device through the aperture 146. In addition to the funneling function that may be realized by the inclusion of the beveled aperture 146, the aperture 146 may also provide the cap 130 with a number of additional desired characteristics. For example, because the aperture 146 is formed in the relatively rigid outer shell 136 and because the aperture 146 is generally positioned a distance away from the port 20 (e.g. in FIG. 1), the aperture 146 and/or outer shell 136 may also function as a strain relief that may relieve strain that might otherwise be applied to endoscope 10 (e.g., at port 20), for example, during device exchanges or transfers. Thus, the shear stress that may be generated during device exchanges can be shifted away from endoscope 10, which may improve the ability of cap 130 to maintain a seal at port 20.

In various embodiments, the securing member 140 may be disposed on a bottom surface of the cap 130. The securing member 140 may take any number of a wide array of forms including those disclosed herein. For example, the securing member 140 may include a pair of tabs 150*a*, 150*b*, which may snap onto or otherwise secure to a port 20 (e.g., FIG. 1). Securing the tabs 150*a*, 150*b* onto the port 20 may include, for example, snapping the tabs 150*a*, 150*b* onto a narrowed ring or portion of the port 20. This may include snapping the tabs 150*a*, 150*b* onto the port from a peripheral or side region of the port 20. In addition, a portion of the shell 136 may include a cutout or notch (not shown) that may provide some structural relief for the securing member 140 and may allow the tabs 150*a*, 150*b* to have greater flexibility when securing cap 130 to port 20 than without the relief. The precise form of securing member 140 and/or the tabs 150*a*, 150*b* may vary. For example, a different number of tabs may be utilized, differently shaped tabs may be utilized, and/or a different securing system altogether may be utilized for securing the cap 130 to the port 20. Furthermore, various adaptors may be provided to create a suitable connection between the cap 130 and the port 20 if such a connection cannot be easily made with the tabs 150*a*, 150*b* or another suitable securing member 140.

Locking members 142 may be generally disposed adjacent the top surface of cap 130 and they may be used to secure and/or hold the position of a device (e.g., a guidewire, catheter, etc.) extending through cap 130 into working channel 16. However, locking members 142 may be disposed on any suitable surface of cap 130 and/or shell 136. Locking members 142 may also be integrally formed with shell 136. In addition to holding the position of a device, locking members 142 may also tend to guide these devices away from the center of cap 130 so that other device may gain access to working channel 16 via cap 130. In at least some embodiments, locking members 142 may include one or more bends, hooks, or channels 144 formed therein that a medical device may be wrapped around or pressed against to hold its position. The number of locking members 142 may vary. In some embodiments, one locking member 142 is utilized. In other embodiments, two, three, four, five, six, or more locking members 142 are utilized. In addition, the precise form of locking members 142 may also vary. For example, locking member 142 may or may not include a wing or flap that may tend to direct a device toward locking member 142.

Figure 4:
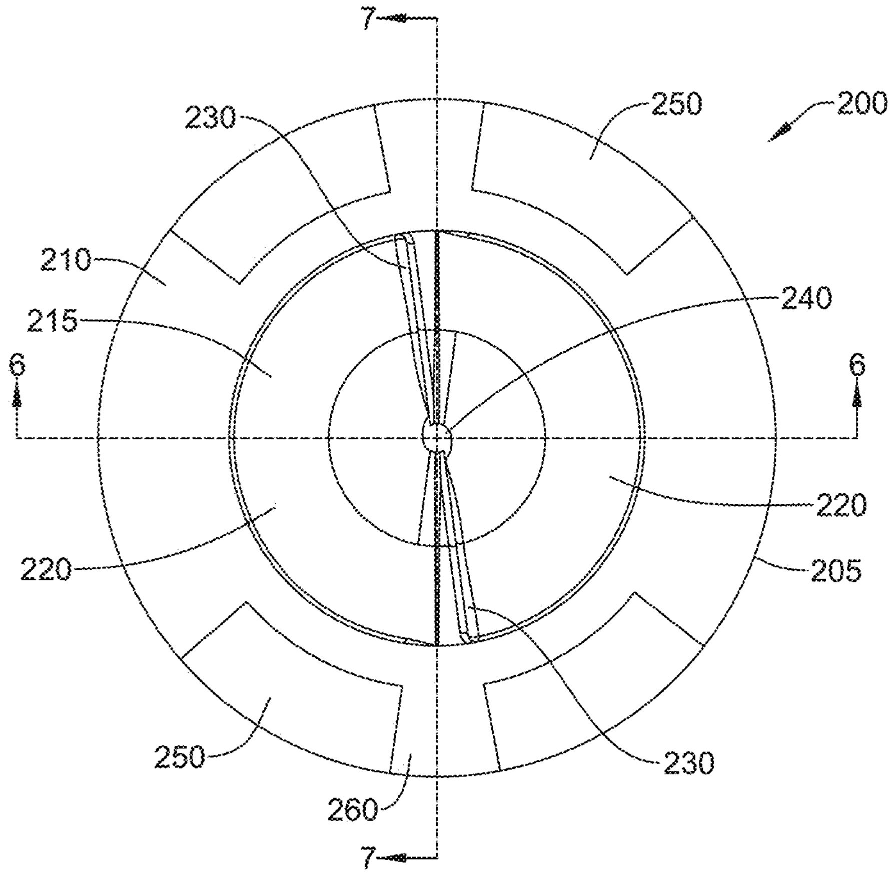
FIG. 4 is a top view of a seal member, according to an embodiment of the present disclosure.
Figure 5:
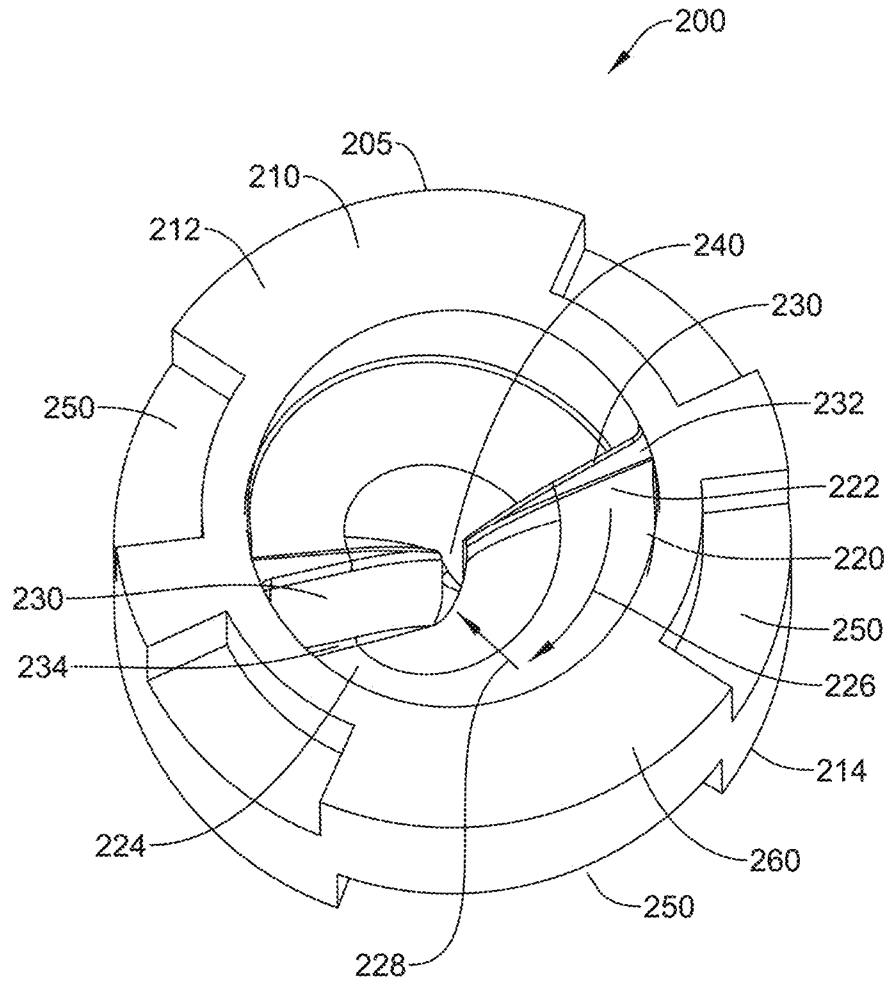
FIG. 5 is perspective top view of the seal member of FIG. 4.

FIG. 4 is a top view of a seal member 200 according to an embodiment of the present disclosure that may be disposed within the cap 130 shown in FIG. 3. The seal member 200 may include a main body 205 defined by a circumferential outer wall 210 surrounding a central lumen 215. At least one axial support wall 230 may extend radially from the outer wall 210 into the central lumen 215. At least one helical flap 220 may extend from the top surface 232 of the support wall 230 helically downward along an inner surface of the outer wall 210 to a bottom surface 234 of the support wall 230, as shown in FIG. 5. The helical flap 220 and the support wall 230 do not extend all the way to the center of the lumen 215 but leave an opening 240 that extends completely through the seal member 200. Accordingly, medical device(s) may be advanced through aperture 146 in the cap 130 shown in FIG. 3, into the lumen 150 in the seal member 200, through opening 240, and into working channel 16 for use as part of a medical intervention. Alternatively, the helical flap 220 and the support wall 230 may extend to the center of the lumen 215 while allowing an instrument to pass through the lumen 215 (e.g., by the helical flap 220 and/or the support wall 230 flexing and/or tearing).

In the embodiment shown in FIG. 4, the seal member 200 includes only two support walls 230 disposed opposite one another, and only two helical flaps 220, each extending helically from one of the two support walls 230. Each helical flap 220 may extend from a first end 222 at the top surface 232 of the support wall 230, helically downward to a second end 224 at the bottom surface 234 of the opposite support wall 230, as shown in FIG. 5. The downward direction may be defined as extending from a top surface 212 to a bottom surface 214 of the main body 205. Each helical flap 220 may extend downward in two directions: helically along the outer wall 210 in the direction shown by first arrow 226, and radially towards the opening 240 in the direction shown by second arrow 228. The downward sloping helical flaps 220 may help guide or funnel devices through the opening 240. The support walls 230 may extend vertically, along a longitudinal axis extending through the opening 240. The two support walls 230 may be disposed opposite each other, with the helical flaps 220 each defining substantially half of the circular seal member 200.

In the embodiment shown in FIGS. 4 and 5, seal member 200 with only two support walls 230 and only two helical flaps 220 may provide an advantage over seal members with more than two support walls and helical flaps. For example, the inclusion of only two support walls 230 and two helical flaps 220 may allow for an increased thickness of the flaps along their cross-section by 10-20%, which may improve sealing performance. Further, the number of potential pockets formed at the bottom of the flap and support wall is reduced. These pockets may become deeper when the angle between the flap and support wall is lower. Reducing the number of support walls and flaps to only two results in a reduced pocket depth because the angle between the flap and support wall increases, which significantly reduces the occurrence of device obstruction and improves device passability, or the ability of devices to translate through the seal member 200.

In various embodiments, the outer wall 210 of the seal member 200 may include a series of alternating grooves 250 and legs 260 in both the top and bottom surfaces. The grooves 250 and legs 260 allow two or more seal members 200 to be stacked (e.g., axially with each other). In some embodiments, the grooves 250 and legs 260 may be uniformly sized and equally spaced around the outer wall 210 (not shown), allowing two seal members 200 to be stacked in any of four 90 degree offset orientations. For example, with the two opposing support walls 230 of each seal member 200 stacked over each other (a "minus" or dash symbol configuration that is the same when one seal member is rotated 180 degrees), and with the two opposing support walls 230 of one seal member 100 oriented perpendicular to the support walls 230 of the second seal member 200 (a "plus" or cross symbol configuration that is the same when one seal member is rotated 90 degrees). In other embodiments, the grooves 250 and legs 260 may be spaced non-equidistant (see FIG. 5) and sized such that two seal members 200 may be stacked in only two 180 degree offset orientations. Sizing and spacing the grooves 250 and legs 260 such that two seal members 200 can only be stacked in the "plus" configuration provides better sealing with similar performance (e.g., passability) of medical devices being able to pass through the seal members 200 as compared to the "minus" configuration.

Figure 6:
FIG. 6 is a cross-sectional side view of the seal member of FIGS. 4 and 5, taken along line 6-6.
Figure 6:
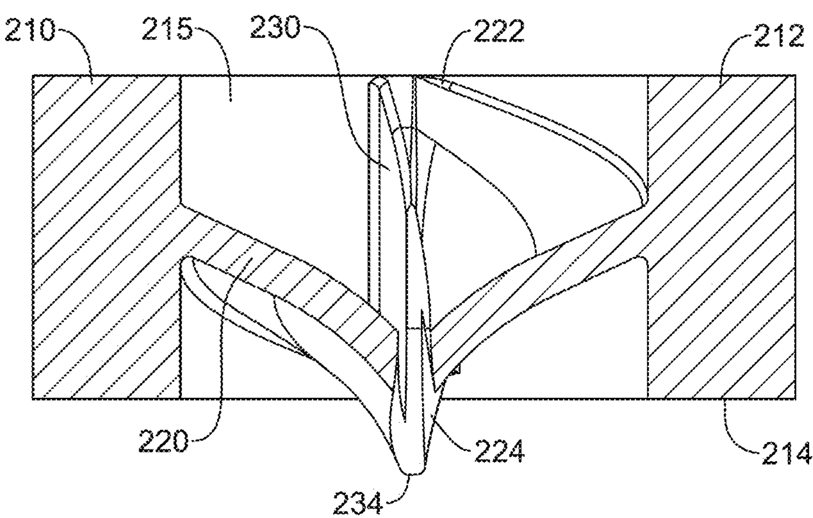
Figure 7:
FIG. 7 is a cross-sectional side view of the seal member of FIGS. 4-6, taken along line 7-7.
Figure 7:
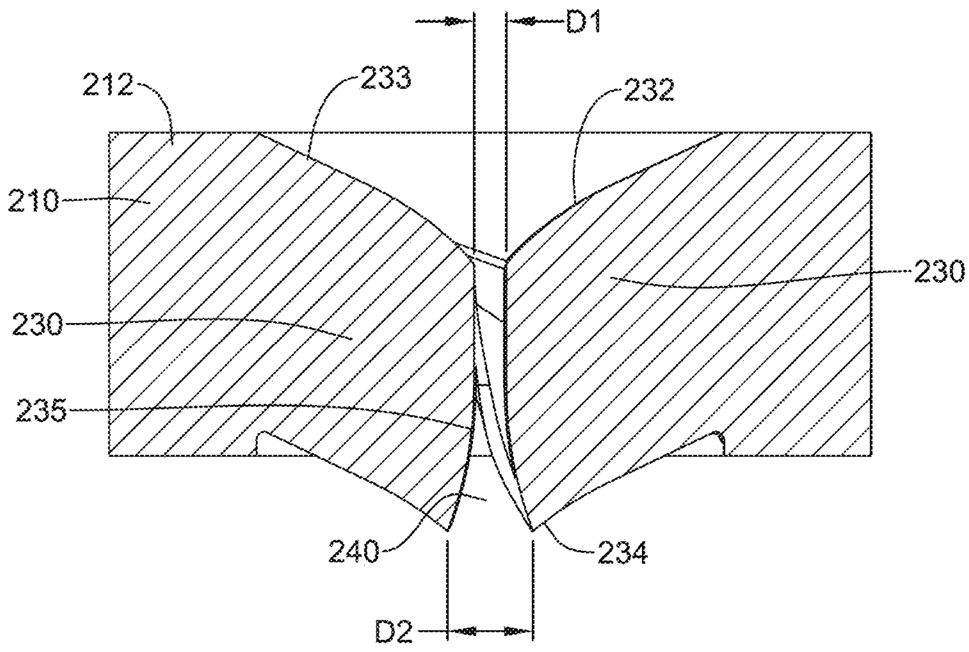

Referring to FIG. 6, a cross-sectional view of the seal member of FIGS. 4 and 5 is illustrate with the helical flaps 220 extending helically downward from the first end 222 at the top surface 212 of the main body 205 to the second end 224 adjacent the bottom surface 234 of opposite support wall 230. The bottom surface 234 of each support wall 230 extends below the bottom surface 214 of the seal member 200. FIG. 7 shows the cross-sectional view rotated 90 degrees from FIG. 6, taken through each of the opposing support walls 230. In FIG. 7, the variable diameter of the opening 240 adjacent the support walls 230 is shown. The support walls 230 may angle downward from a base 233 connected to the outer wall 210 to an inner edge 235 that partially defines the opening 240. The opening 240 increases from a first diameter D1 between facing support walls 230 adjacent the top surface 232 of the support walls 230 to a second diameter D2 at the bottom surface 234 of the support walls 230. The increasing hole diameter at the bottom of the seal member 200 prevents the formation of a pocket which may obstruct the introduction of a curved tip medical device. The reduced diameter D1 at the top compensates for the larger bottom diameter D2 of the opening 240, thus maintaining the sealing properties of the seal member 200.

The seal member 200 illustrated in FIGS. 4-7 may be a single monolithic piece formed by injection molding or other suitable molding techniques. The seal member 200 may be made of an elastomeric material such as a flexible silicone.

Figure 8:
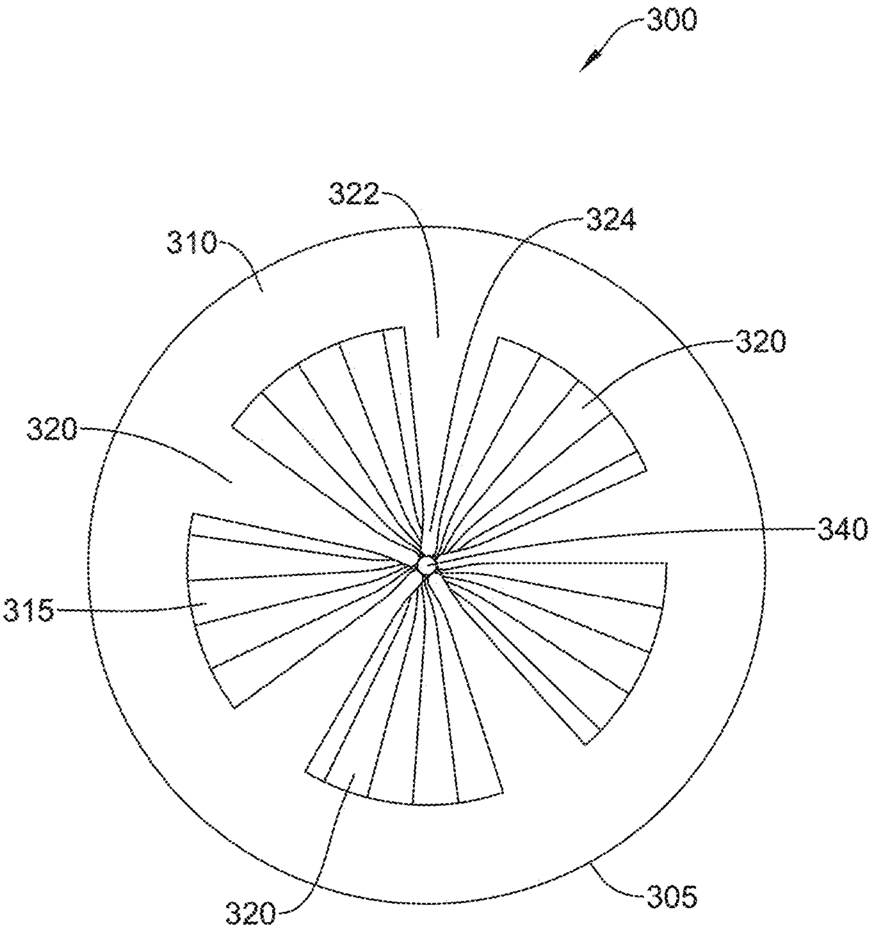
FIG. 8 is a top view of a seal member, according to an embodiment of the present disclosure.

FIG. 8 shows a top view of a seal member 300 in accordance with an embodiment of the present disclosure that may be disposed within the cap 130 shown in FIG. 3. The seal member 300 may include a main body 305 defined by a circumferential outer wall 310 surrounding a central lumen 315. A plurality of projections 320 may extend radially inward from the outer wall 310 towards a center of the lumen 315. The projections 320 may extend from a base 322 attached to the outer wall 310 to a tip 324. The tips 324 of the projections 320 do not meet at the center of the lumen 315 but leave an opening 340 that extends completely through the seal member 300. Accordingly, medical device(s) may be advanced through aperture 146 in the cap 130 shown in FIG. 3, through opening 340, and into working channel 16 for use as part of a medical intervention. Alternatively, the helical projections 320 may extend to the center of the lumen 315 while allowing an instrument to pass through the lumen 315 (e.g., by the projections 320 flexing and/or tearing).

Figure 9:
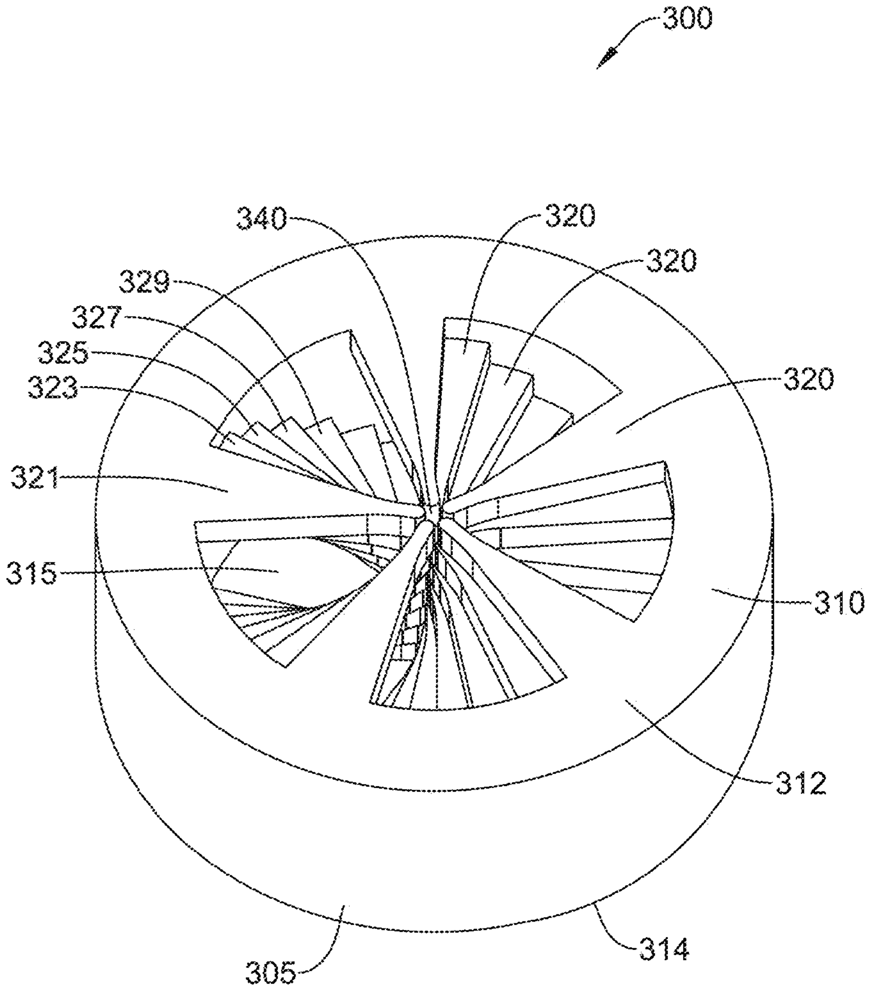
FIG. 9 is a perspective top view of the seal member of FIG. 8.

In various embodiments, the plurality of projections 320 may be oriented in a series of circumferentially and angularly offset layers such that they spiral downward around the seal member 300 from the top surface 312 to the bottom surface 314 of the outer wall 310, in a staircase manner as shown in FIG. 9. Each layer may include the plurality of circumferentially spaced apart projections 320. The series of offset layers may extend axially along the main body 305 with a first layer 321 defining a portion of the top surface 312 of the main body, a second layer 323 disposed under and circumferentially offset from the first layer 321, a third layer 325 disposed under and circumferentially offset from the second layer 323, a fourth layer 327 disposed under and circumferentially offset from the third layer 325, a fifth layer 329 disposed under and circumferentially offset from the fourth layer 327, etc. The bottom layer may define a portion of the bottom surface 314 of the main body 305.

The seal member 300 may include any number of projections 320. In some embodiments, the seal member 300 may include a plurality of layers each including, e.g., three to fifteen circumferentially spaced apart projections 320 arranged equidistant around the circumference of the main body 305. The seal member 300 may include, e.g., three to fifteen layers of projections. In the example shown in FIG. 9, the main body 305 includes seven layers each having five projections.

Figure 10:
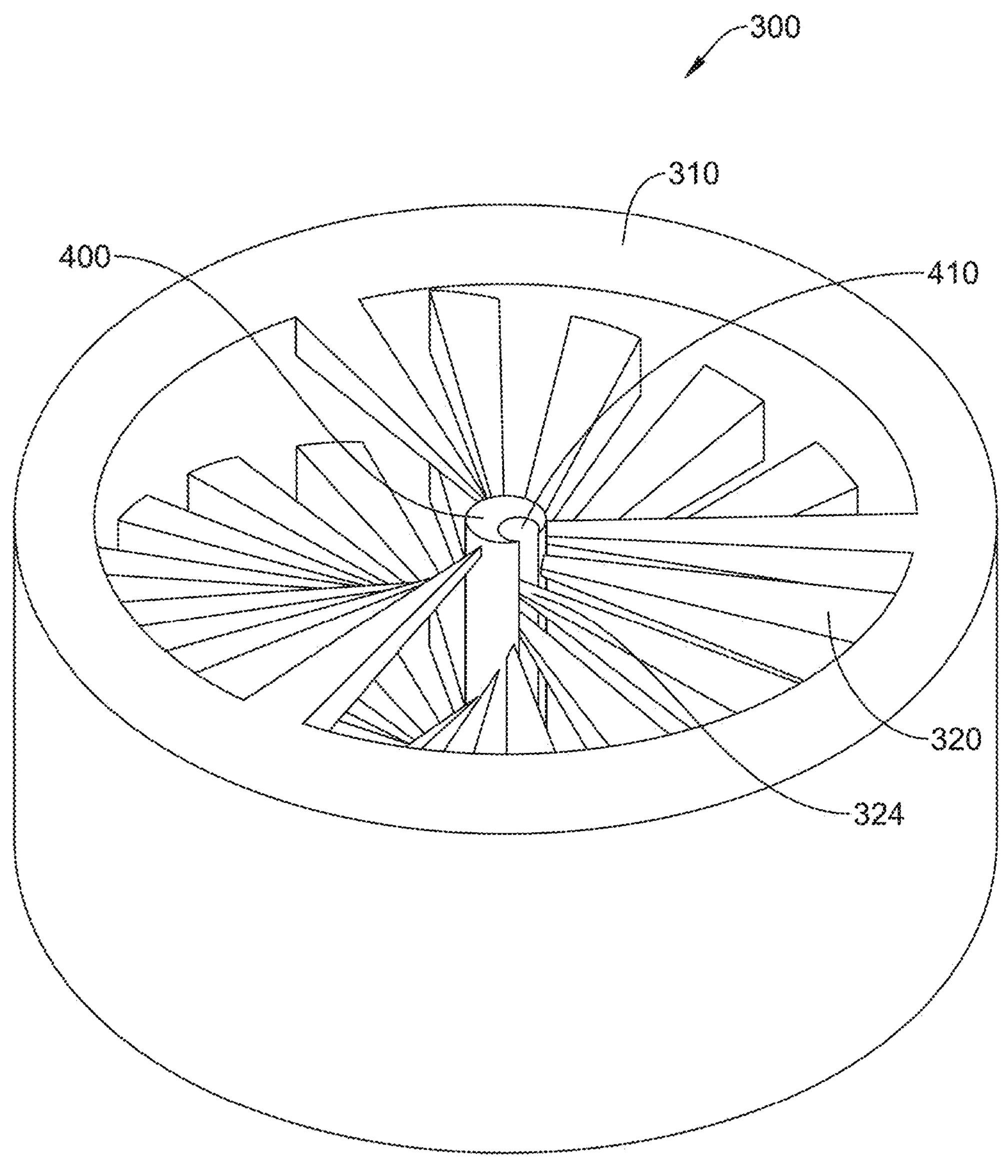
FIG. 10 is a perspective top view of the seal member of FIGS. 8 and 9 with a medical device inserted therethrough.

A medical device may be inserted through the opening 340 in the seal member 300 and the tips 324 of the projections 320 may engage the medical device to form a seal. The seal member 300 may provide an improved seal against a catheter or other medical device having a longitudinal slit or channel, especially a C shaped longitudinal channel. When a device 400 having a C-shaped channel 410 is inserted through the opening in the seal member 300, the tips 324 of the projections 320 may enter the channel 410 of the device 400, providing an enhanced seal, as shown in FIG. 10. The plurality of projections 320 disposed circumferentially around the outer wall 310 and extending radially inward may provide the advantage of engaging the channel 410 regardless of the rotational orientation of the device 400. Also, when the device 400 is rotated while disposed in the seal member 300, the channel 410 will remain sealed because while some projection tips 324 will slip out of the channel 410 as the device 400 rotates, adjacent projection tips 324 will enter and seal the channel 410. In some embodiments, the projection tips 324 may be sized and shaped to match the dimensions of the channel 410 of a particular device 400.

Figure 11:
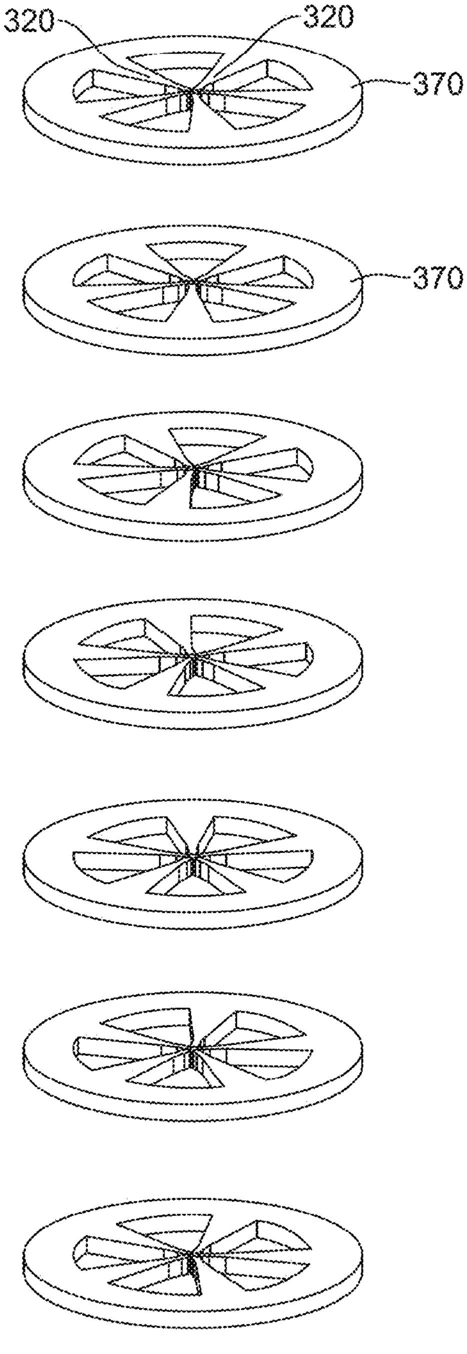
FIG. 11 is a perspective view of separate discs used to manufacture or assemble the seal member of FIGS. 8-10, according to an embodiment of the present disclosure.

A seal member 300 may be manufactured and/or assembled using a variety of methods. In one example, the seal member 300 may be molded as a plurality of separate discs 370 as shown in FIG. 11. In various embodiments, each disc 370 may be molded with, e.g., 5 projections 320 (although other numbers of projections 320 are contemplated as discussed above) each having a tip 324 with a dimension sized to engage the C-channel. The discs 370 may be stacked one above another with each disc clocked at an angle to cover the entire 360° periphery around the opening 340. The stacked discs may then be bonded together to form the seal member 300. While this stacking process results in a seal member 300 having the desired sealing properties, the method of individually molding each disc and then assembling them into the seal member 300 may be time-consuming as this method calls for expensive assembly automation process, since manual assembling is not feasible. Additionally, controlling the angular orientation of each disc during assembly may be expensive and challenging. All of these factors may bring up the cost of assembly and reduce yield.

Molding the seal member 300 with all projections 320 facing inward in a single molded component, however, may be difficult due to the many needed undercuts and restriction of tool movement. Additionally, dissolving core-molding processes may increase the cost and impact the quality of the component.

Figure 12:
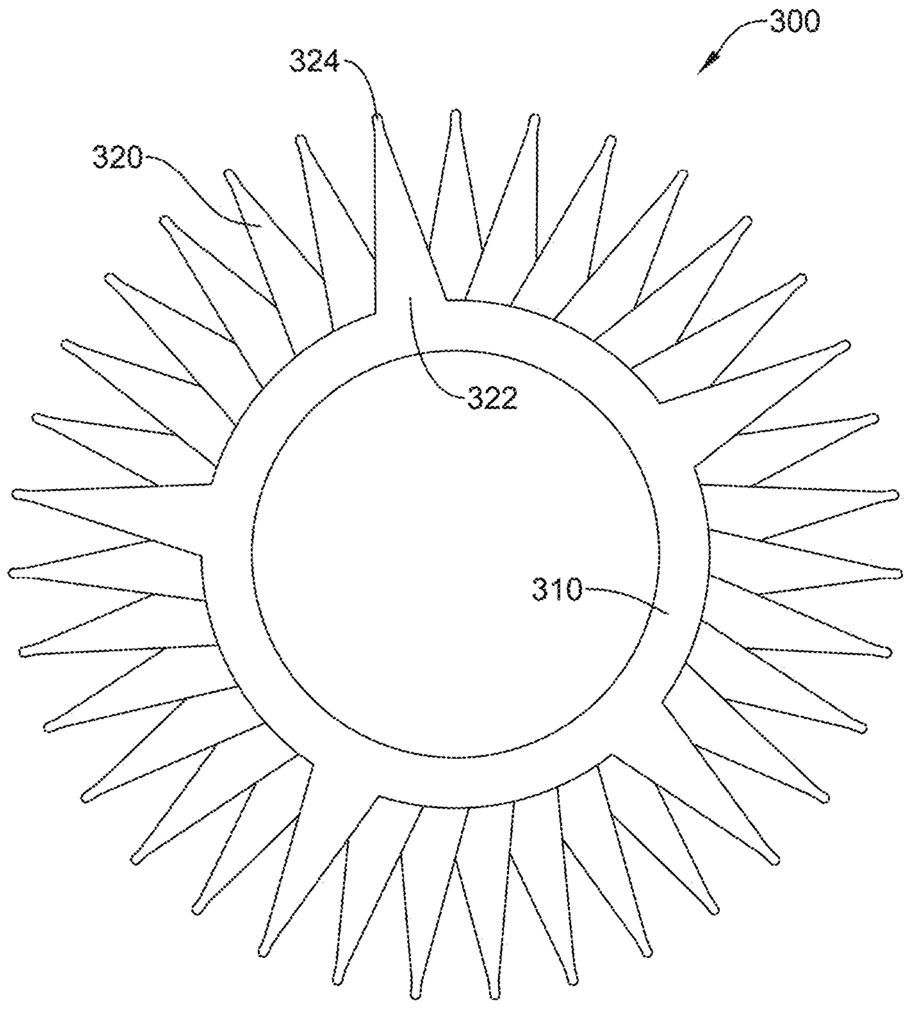
FIG. 12 is a top view of an example seal member after molding and before being turned inside out, according to an embodiment of the present disclosure.
Figure 13:
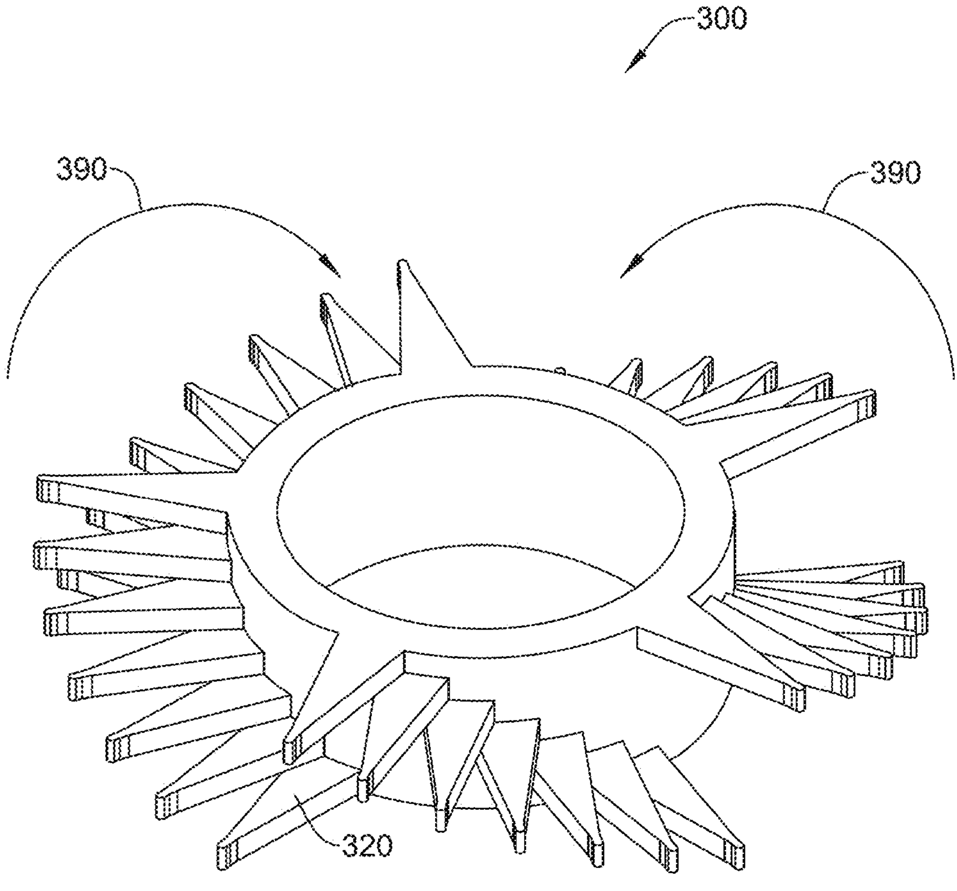
FIG. 13 is a perspective view of the seal member of FIG. 12.
Figure 14:
FIG. 14 is a perspective view of a seal member after molding and before being turned inside out, according to an embodiment of the present disclosure.
Figure 14:
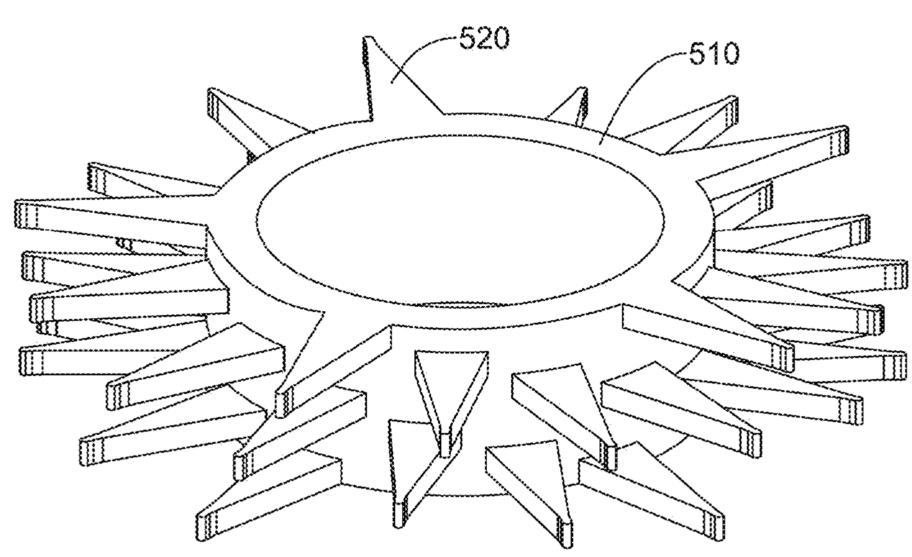

In an embodiment, an entire seal member 300 may be molded in a single monolithic piece in a simple, cost-effective process. The seal member 300 may be molded with the base 322 of all the projections 320 disposed on the outer periphery of the outer wall 310 and the tips 324 of the projections 320 extending radially outward, as shown in FIG. 12. The projections 320 may be arranged in a series of circumferentially offset layers. In the example shown in FIG. 13, each layer has five projections 320 and there are seven layers of projections, with each layer offset circumferentially from the layers above and below. This orientation forms a staircase of projections 320. After unmolding, the seal member 300 is turned inside out, turning the projections 320 in to the center, as indicated by arrows 390. The resulting structure is as shown in FIG. 9. The layers of projections 320 may be offset in a variety of patterns. In some embodiments, each layer of projections may be offset circumferentially by between 5 and 40 degrees from adjacent layers. In the example shown in FIG. 13, the layers of projections may be offset circumferentially by 11 degrees from the adjacent layers above and/or below. In another example, shown in FIG. 14, a seal member 500 may have seven layers of projections 520 offset circumferentially by 22 degrees from the adjacent layers above and/or below.

Figure 15:
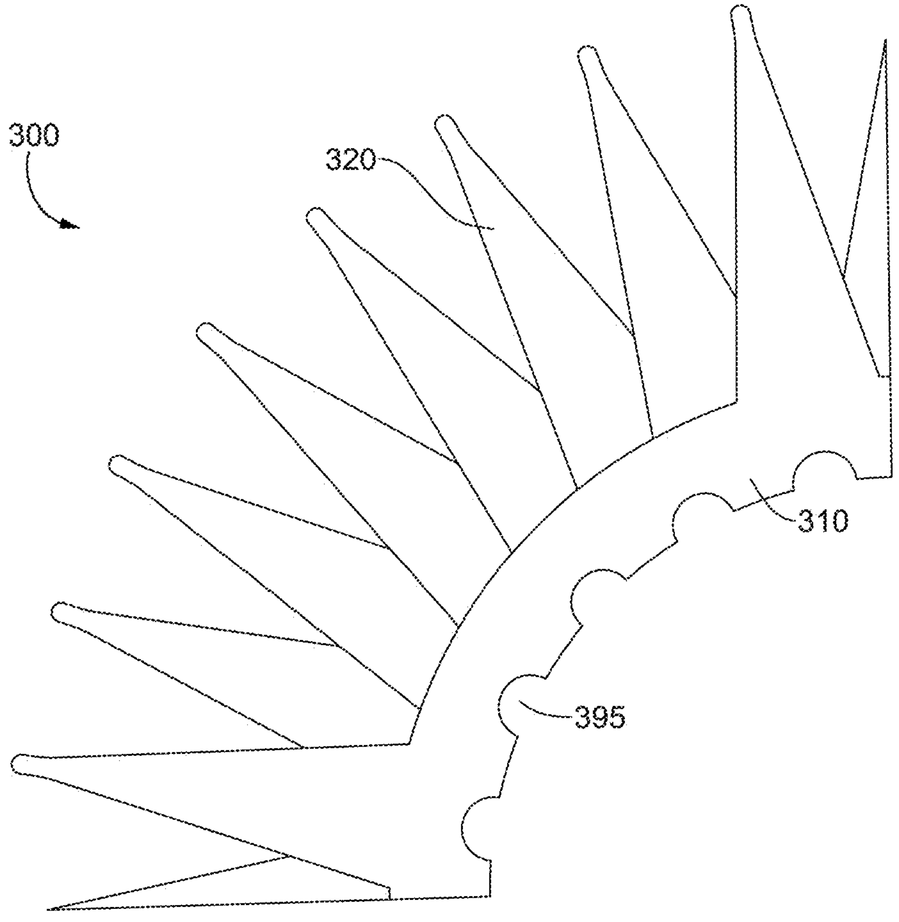
FIG. 15 is a partial top view of a seal member after molding and before being turned inside out, according to an embodiment of the present disclosure.

In an embodiment, the outer wall 310 of a seal member may include one or more axial grooves or slits 395 formed on the inner surface during molding, as shown in FIG. 15. The slits 395 are on the outer surface of the outer wall 310 after the seal member 300 is turned inside out and may provide stress relief for the completed seal member 300. The slits 395 may prevent or assist in the reduction of warping of the seal member 300 after it is turned inside out.

Figure 16:
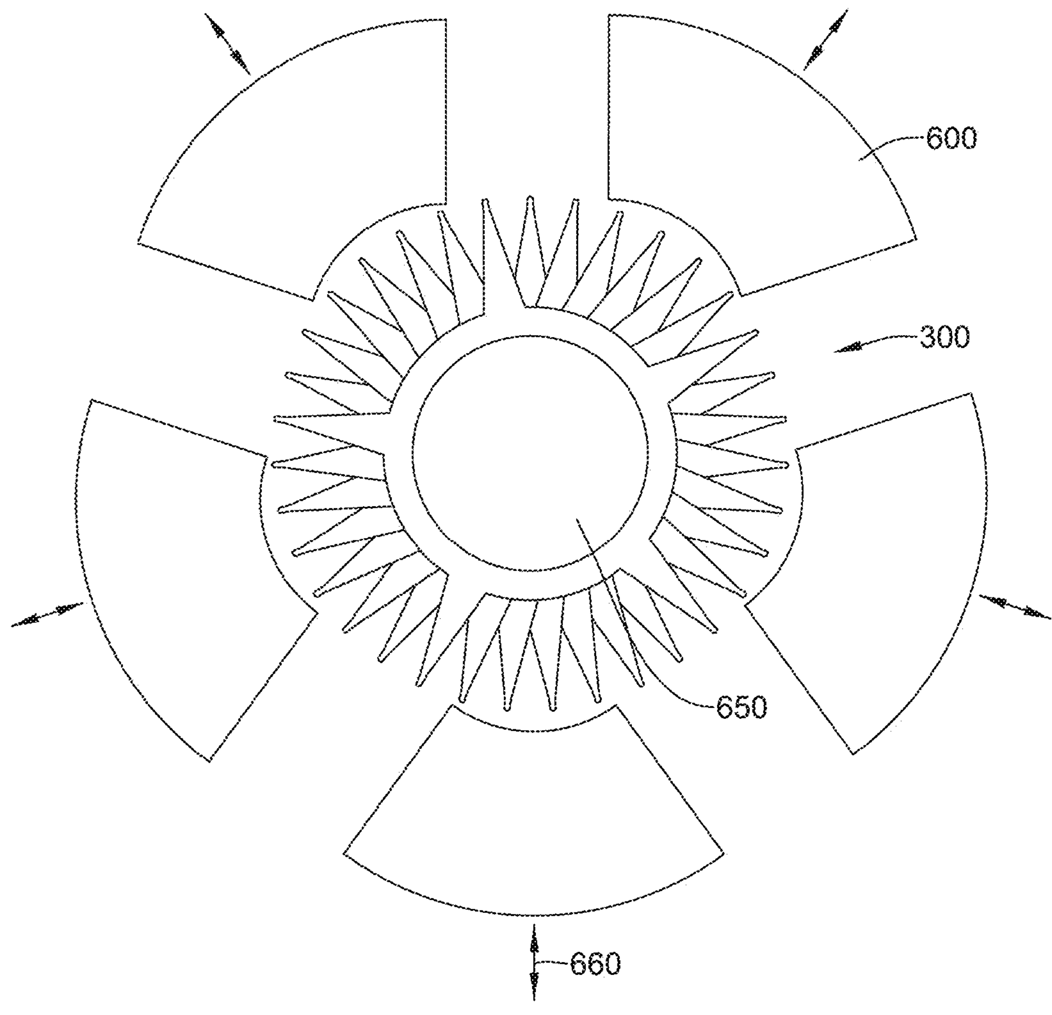
FIG. 16 is a top view of a mold with a seal member disposed therein, according to an embodiment of the present disclosure.
Figure 17:
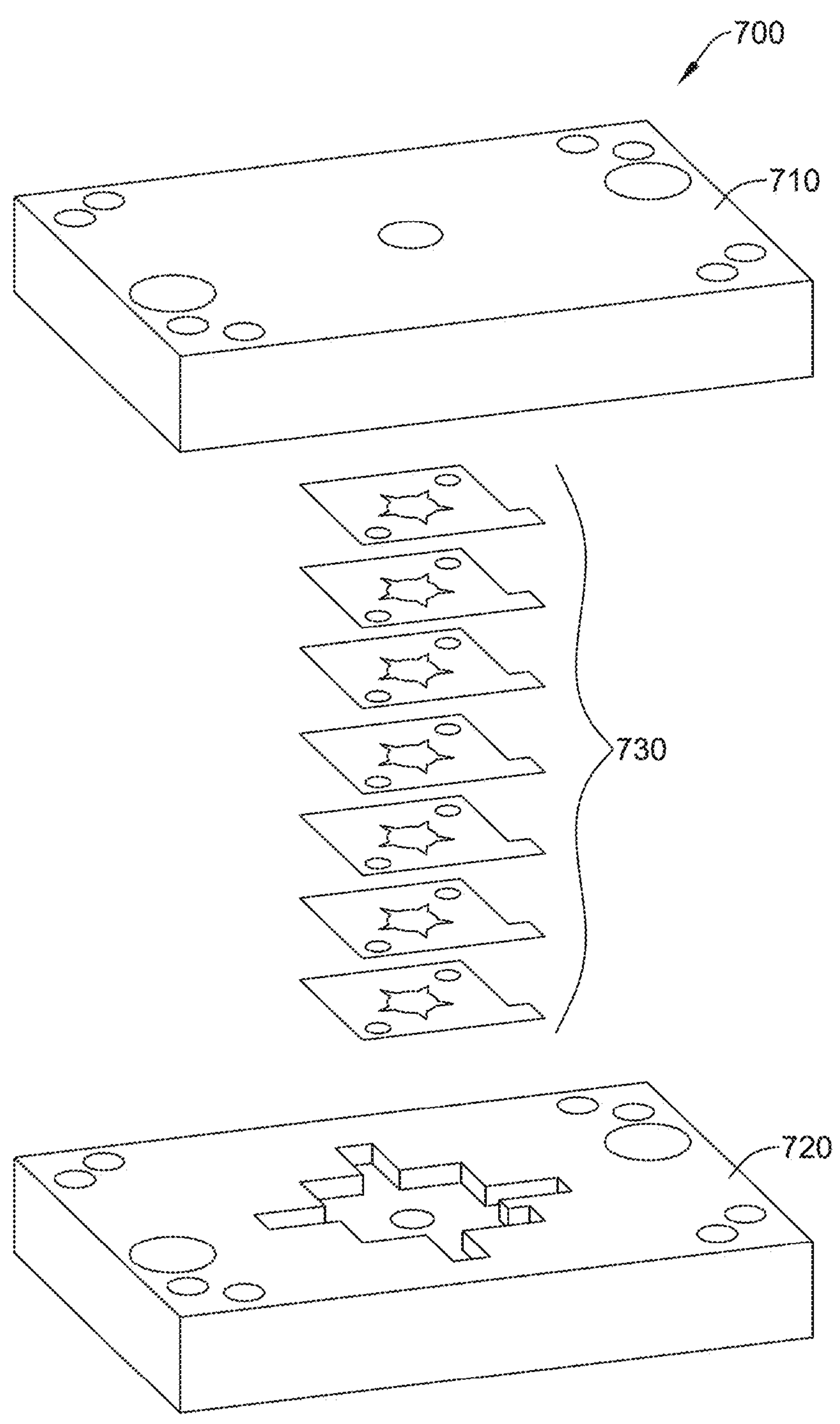
FIG. 17 is a perspective view of a mold for seal member prior to assembly, according to an embodiment of the present disclosure.

An inside out seal member 300 with projections 320 in any orientation may be manufactured by an injection molding process. In an embodiment, the seal member 300 may be formed using a radially ejectable mold 600 as shown in FIG. 16. The radially ejectable mold 600 may include a plurality of radially moveable segments and a core element 650. The desired projection number and orientation is formed in the mold segments, which are removed radially to unmold the seal member 300, as indicated by arrows 660. The size of the core element 650 determines the dimensions of the outer wall 310 of the seal member 300. In various embodiments, the seal member may be formed using an axially staked mold 700, such as shown in FIG. 17. The axially staked mold 700 may include a top 710 and a base 720 and a series of staked projection orientation plates 730, each plate 730 defining the shape and orientation of one layer of projections 320.

In various embodiments, a seal member 100, 200, 300 may comprise a soft material such as a plastic, foam, silicone, rubber, or elastomer that may be suitable for sealing about a medical device extending therethrough. The precise form and materials for a seal member 100, 200, 300 may vary. For example, a seal member 100, 200, 300 may include a pliable or formable material that may or may not be absorbent. In some embodiments, a seal member 100, 200, 300 may include those materials used for similar structures disclosed in U.S. Pat. No. 6,663,598, filed May 17, 2000 and titled "Fluid Seal For Endoscope," the disclosure of which is herein incorporated by reference in its entirety and for all purposes. In at least some embodiments, a seal member 100, 200, 300 may extend laterally to the edges (and/or the top) of a shell 136, thereby substantially filling an inner chamber 132. This may help to prevent or reduce the amount of fluids that may migrate into and out from cap 130. Alternatively, a gap may be formed between the top of seal member 100, 200, 300 and the top of the inner chamber 132 of shell 136 and may be used, for example, to hold bodily fluids that may escape from seal member 100, 200, 300 and that may otherwise "splash" during, for example, device removal or exchange. In still further embodiments, a portion of seal member 100, 200, 300 may extend out from shell 136 and it may define or otherwise function as a strain relief.

In addition to being disposed in a biopsy cap 130 for an endoscope, a seal member 100, 200, 300 may be applied to other similar applications as well where leakage prevention is required along device(s) inserted through the seal member 100, 200, 300. Additionally, having downwards oriented flaps, the seal member 200 may also act as a one-way valve for sealing fluid inside the seal member 200.

Figure 18:
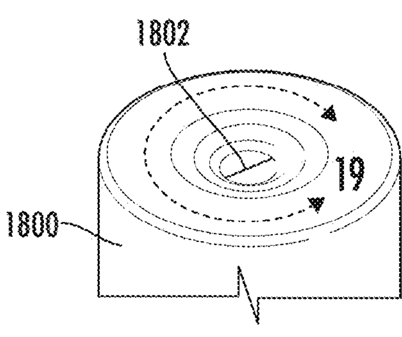
FIG. 18 illustrates an isometric view of a biopsy cap.

With reference to FIG. 18, an isometric view of a biopsy cap 1800 is illustrated. The biopsy cap 1800 can be installed in-line with an inlet of a working channel (e.g., as illustrated in FIGS. 1 and 2). The biopsy cap 1800 includes an aperture 1802, which is a substantially linear, one-dimensional slit. The aperture 1802 is in a substantially closed configuration without any open space between the walls of the aperture 1802. The aperture 1802 is ready for one or more medical instruments to be passed through the aperture 1802.

Figure 19:
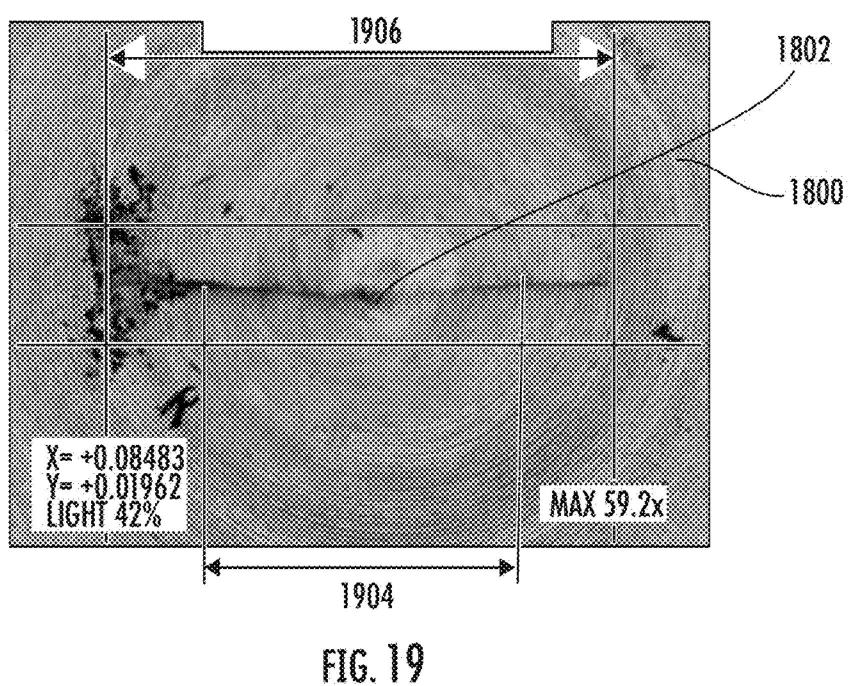
FIG. 19 illustrates a magnified view of the aperture of a used biopsy cap of FIG. 18.

With reference to FIG. 19, a magnified view of the aperture 1802 of the used biopsy cap 1800 of FIG. 18 is illustrated. The aperture 1802 of the biopsy cap 1800 extends substantially linearly across a portion of the biopsy cap 1800. The aperture 1802 has a length 1906 after being used in the procedure, which is larger than an original length 1904. During use of the biopsy cap 1800, one or more medical instruments may have been inserted into the linear ends of the aperture 1802, causing the aperture 1802 to tear further along the biopsy cap 1800 such that the length of the aperture 1802 extended from the original length 1904 to the enlarged length 1906, decreasing the sealing strength of the biopsy cap 1800 and increasing the ease of passage through aperture 1802 compared to the pre-torn aperture 1802.

Figure 20A:
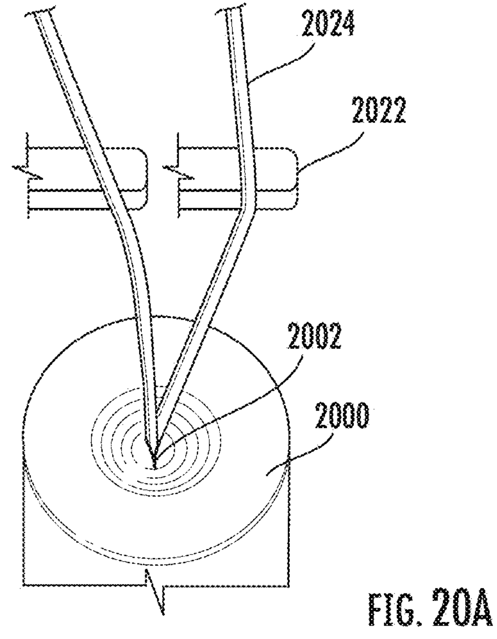
FIG. 20A illustrates a biopsy cap with two guidewires extended through the biopsy cap.
Figure 20B:
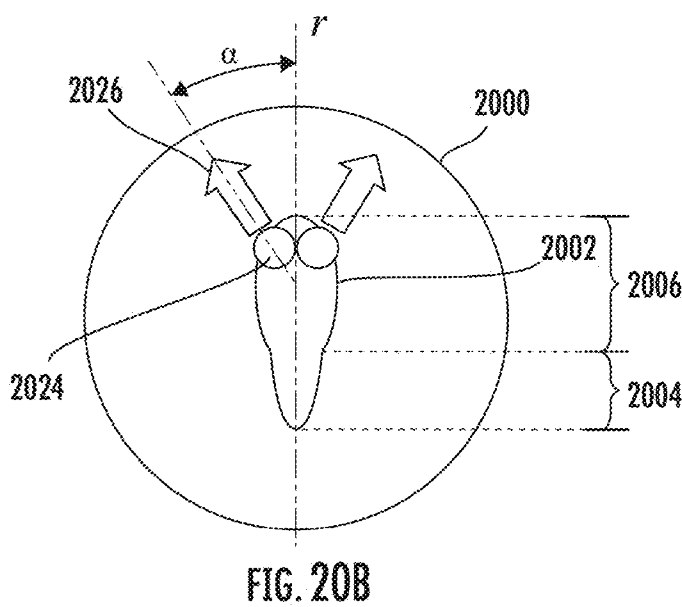
FIG. 20B illustrates a top cross-sectional view of the biopsy cap of FIG. 20A.

With reference to FIGS. 20A and 20B, a biopsy cap 2000 is illustrated, which includes two guidewires 2024 extending through an aperture 2002 according to an embodiment of the present disclosure. The guidewires 2024 extend away from the aperture 2002 and are guided by guide members 2022. The guidewires 2024 are forced against the walls of the aperture 2002 generally in the direction of the vectors 2026 shown in FIG. 20B. Because these vectors 2026 extend in a direction that is a number of degrees a away from an axis r of the aperture 2002, the aperture 2002 is pulled open at least at the end of the aperture 2002 with the guidewires 2024. FIG. 20B illustrates that the guidewires 2024 have torn the aperture 2002 in multiple directions, causing a first portion 2004 of the aperture 2002 to open and a second portion 2006 to open with a widening tear. The first portion 2004 of the aperture 2002 is undesirably open, allowing for the possible exchange of fluids through the aperture 2002, while the second portion 2006 is torn to a wider opening than the first portion 2004, allowing for even more fluids to be exchanged through the aperture 2002.

In various embodiments, a longer linear length of an aperture may be desirable to decrease the axial force required to insert and remove medical devices through the aperture when compared to a shorter linear length of an aperture. However, because a longer linear length of an aperture may be less able to prevent fluid exchanges through the aperture when compared to a shorter linear length of an aperture, a shorter linear aperture may be reinforced to accomplish both purposes, e.g. assist in allowing sealable access for instruments, while reinforcing the aperture against tearing to inhibit or prevent the exchange of fluids. For example, an aperture may have an amount of resistance to the insertion of medical devices such that at the same time there is generally a seal against the exchange of fluids across the aperture and/or such that medical devices may be wiped of fluids when being removed from the working channel and through the aperture. An exemplary amount of force applied from a medical professional for passing one or more medical devices through an aperture, in the context of a biopsy cap used with a working channel in endoscopic procedures, may be from about 0.5 lbf to about 3.5 lbf.

Figures 21A, 21B, 21C:
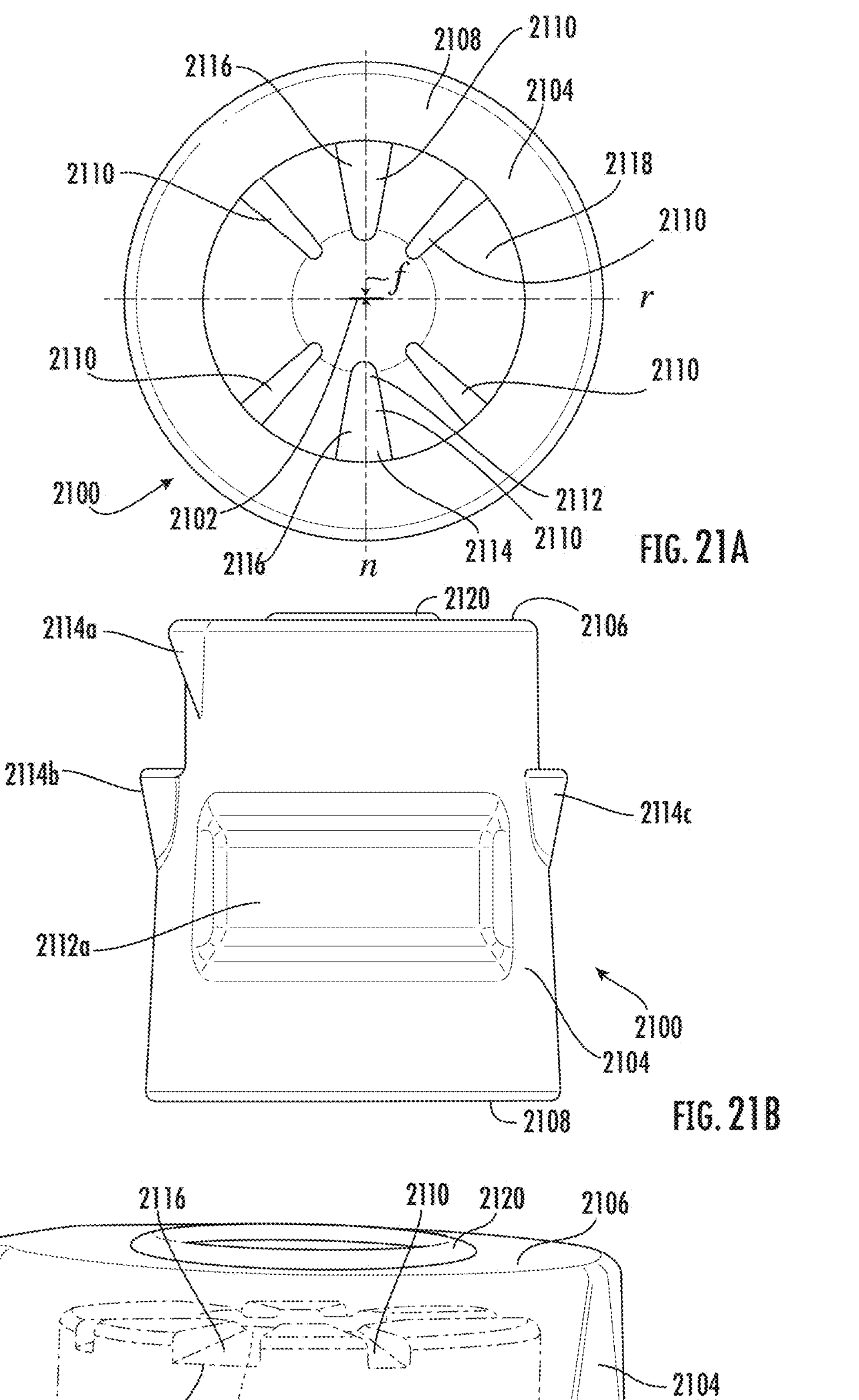
FIG. 21A illustrates a bottom view of a biopsy cap including ribs, according to an embodiment of the present disclosure.
FIG. 21B illustrates a side view of the biopsy cap of FIG. 21A.
FIG. 21C illustrates a translucent substantially side-view of the biopsy cap of FIGS. 21A and 21B.

With reference to FIGS. 21A-21F, an embodiment of a device for providing reinforced sealable access to a working channel is illustrated, which includes a biopsy cap 2100 with a tubular body 2104 having a proximal end 2106, a distal end 2108 and extending along a longitudinal axis. The distal end 2108 is configured to be installed in-line with the working channel at a proximal end or inlet port of the working channel. The biopsy cap 2100 includes a substantially linear aperture 2102 at the proximal end 2106 of the body 2104. The aperture 2102 extends along a centerline axis r that is perpendicular to a longitudinal axis of the tubular body 2104 and is configured to allow one or more medical instruments to be passed therethrough and, at the same time, substantially seal against fluids from the working channel passing therethrough. Six reinforcing ribs 2110 are arrayed about the aperture 2102. The ribs 2110, shown from a bottom view of the biopsy cap 2100 in FIG. 21A, are disposed on and extend distally along the longitudinal axis from a surface 2118 that is internal to the tubular body 2104. The ribs 2110 extend in a plane substantially perpendicular to the longitudinal axis. The ribs 2110 that are farthest away from the normal axis n may be arranged about 15° to about 75°, or about 45° from the normal axis n or the axis r. The ribs 2110 act to reinforce the aperture 2102 in the closed position assisting the aperture 2102 to resist fluid pressure and exchange across the aperture 2102. The arrangement and number of the ribs 2110 closer to the axis n increase stiffness of the biopsy cap 2100 along the axis n relative to the stiffness of the biopsy cap 2100 along the axis r. This increased stiffness along the axis n (compared to a stiffness along the r axis) also assists in providing a resistive force f along axis n. Resistive force f may be described as a force vector acting in a direction perpendicular to the axis r. The resistive force f may resist a force created by an object (e.g., a guidewire or another instrument being passed through the aperture 2102). There are also no ribs 2110 arranged and extending substantially along the axis r. This is done as well to promote stiffness and closure of aperture 2102 of the biopsy cap 2100 substantially along the direction of axis n relative to the stiffness and closure of the aperture 2102 along the axis r. Any forces (e.g., as applied by a guidewire or an instrument) substantially along the axis n that may cause opening and/or tearing of the aperture 2102 will engage with portions of the biopsy cap 2100 having a greater stiffness when compared to portions of the biopsy cap 2100 that forces may engage substantially along the axis r. As the ribs 2110 extend radially away from the aperture 2102 from a first end 2112 to a second end 2114, they become wider and thicker (i.e., the ribs 21210 are wider and thicker at the second end 2114 than they are at the first end 2112). The wider and thicker second ends 2114 of the ribs 2110 extending toward the aperture 2102 to the narrower and thinner first ends 2112 contributes to the focused resistive force vectors f directed at the center of the aperture 2102 when compared to uniform width and thickness ribs 2110. Additionally, specific ribs 2116 of the groups of ribs 2110 that are normal to the r axis and extend along the normal axis n are wider than the remaining ribs 2110 that are offset from the normal axis n. Because ribs 2116 are wider than the remaining ribs 2110, they have more volume of material to contribute to the resistive force vectors f in the direction perpendicular to the axis r to promote stiffness and closure of the aperture 2102. Increasing a combined volume of the material of the ribs 2110, e.g., by increasing the width, thickness, or length of one or more ribs 2110, or increasing the number and/or arrangement of ribs 2110 in relation to the axis n can contribute to the resistive force vectors f by providing additional rib(s) 2110 mass in opposition to the force of an instrument in the aperture 2102. These characteristics of the ribs 2110 may be adjusted to "tune" the biopsy cap 2100 to a desired level of resistance to tearing, aperture 2102 closure promotion, amount of fluid exchange, and instrument force necessary to pass an instrument through the aperture 2102. A rib 2110 extending along axis n may contribute to the resistive force vector f more than another rib that is offset from axis n, e.g., a rib 2110 that is angled about 15° to about 75°, or about 45° away from axis n about the longitudinal axis of the biopsy cap 2100. A force required to tear the aperture 2102 of the biopsy cap 2100 having the ribs 2110 is greater than the tear force for the same aperture without the ribs 42110. Although FIGS. 21A and 21C illustrate six ribs 2110, any number of ribs may be included (e.g., 1, 2, 3, 4, 5, 7, 8, 9, 10, 12, 20, 50, 100, etc.). Although these figures illustrate variable width and thicknesses amongst the ribs 2110, the ribs 2110 may be of uniform width and thickness. The ribs 2110 are arranged substantially symmetrical about the axis r such that the resistive force vectors f acting on aperture 2102 are substantially symmetrical. In some embodiments, the arrangement may be asymmetrical. A ridge 2120 is also included as will be described below to assist with reinforcement and resisting tears. The ridge 2120 may be combined with the biopsy cap 2100 or a biopsy cap 2100 may not include the ridge 2120. The ridge 2120 may be disposed radially outside of the ribs 2110 or the ridge may extend through the ribs 2110 (e.g., as shown in FIG. 10 discussed below). The ridge 2120 and/or ribs 2110 may alternatively or additionally be disposed on proximal and/or distal surfaces of a biopsy cap 2100.

Figure 21D:
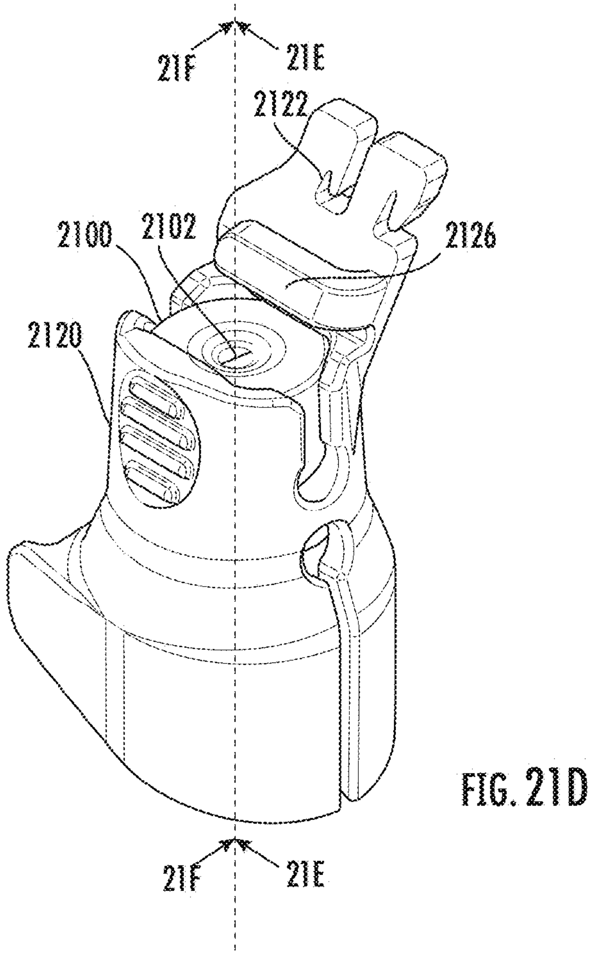
FIG. 21D illustrates an isometric view of the biopsy cap of FIGS. 21A-21C in a housing, according to an embodiment of the present disclosure.
Figure 21E:
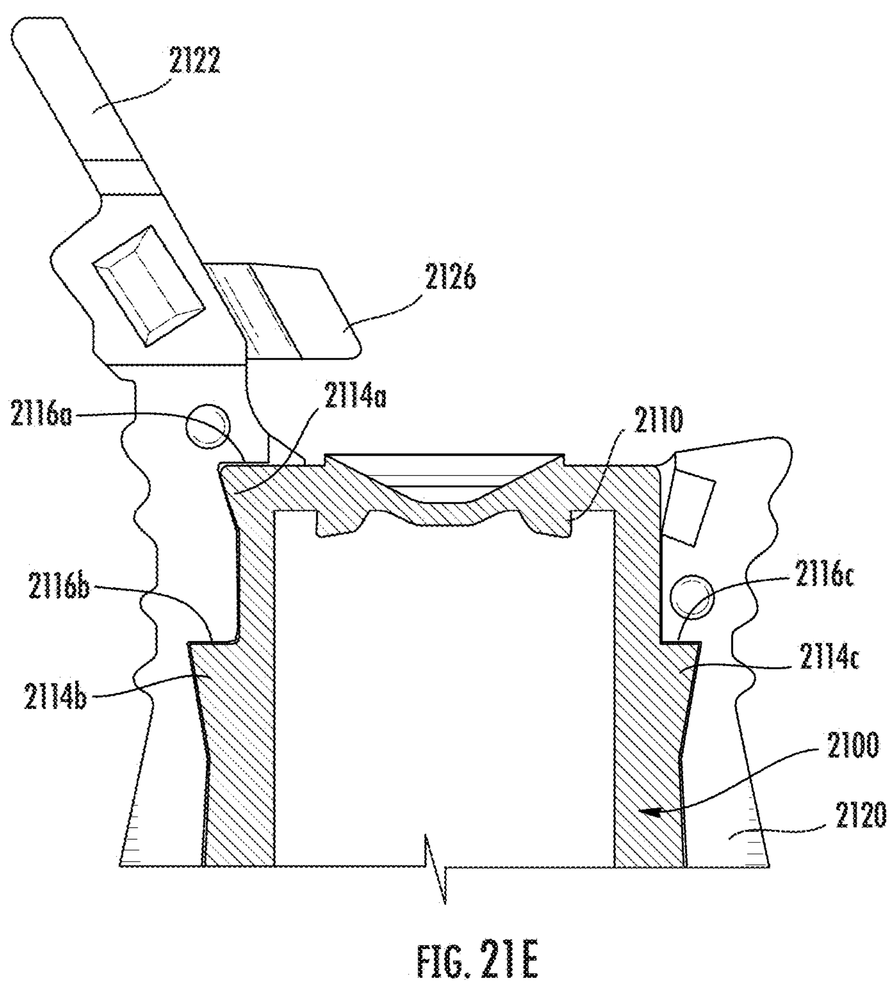
FIG. 21E illustrates a cross-sectional view of FIG. 21D.
Figure 21F:
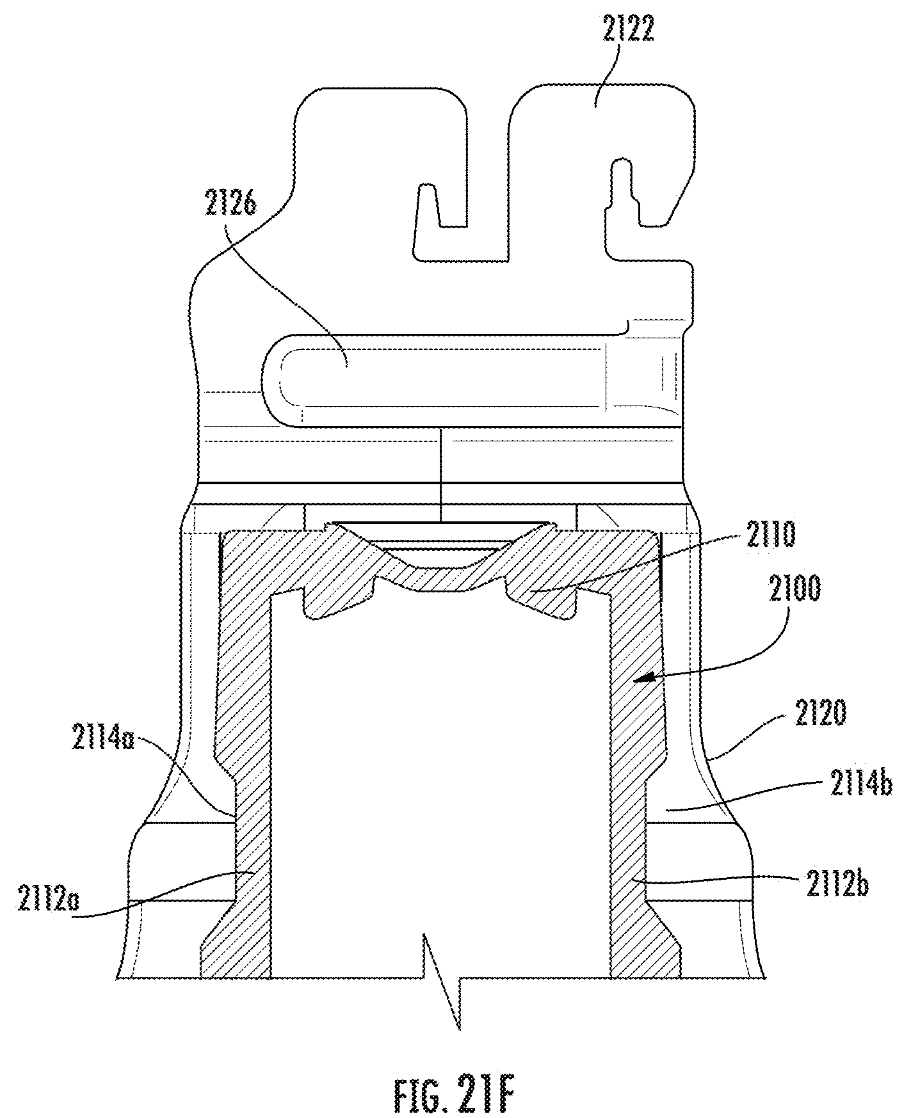
FIG. 21F illustrates a cross-sectional view of FIG. 21D.

With reference to FIGS. 21D-21F, a biopsy cap 2100 is illustrated within an exemplary housing 2120 according to an embodiment of the present disclosure. The housing 2120 includes variable-sized locking channels 2122 for accommodating one or more medical instruments (e.g., a guidewire). Medical instruments may also be assisted by the guide arm 2126. The biopsy cap 2100 also includes a first surface feature 2114*a* attached to or integrally formed with a proximal end of the biopsy cap 2100 and second and third surface features 2114*b*, 2114*c* attached to or integrally formed with the tubular body 2104 of the biopsy cap 2100. These surface features 2114*a*, 2114*b*, and 2114*c* are compressingly and/or frictionally engaging corresponding surface features 2116*a*, 2116*b*, 2116*c* of the housing 2120 that may be a lip, a step feature, or the like, that are integrally formed with an inner wall of the housing 2120. Recessed portions 2112*a*, 2112*b* are integrally formed within the tubular body 2104 of the biopsy cap 2100 and are offset from the surface features 2114*b*, 2114*c* by about 90-degrees relative to an outer circumference of the biopsy cap 2100. Pivot members 2114*a*, 2114*b* (e.g., first pivot button, first pivot feature, etc.) are integrally formed within the housing 2120 and compressingly and/or frictionally engage the corresponding recessed portions 2112*a*, 2112*b*.

In various of the embodiments described here and otherwise, ribs of a device may extend radially in a plane substantially transverse to the longitudinal axis of the device. Each rib of a plurality of ribs may have a width dimension in the transverse plane, and a thickness dimension in a plane substantially parallel to the longitudinal axis. One or more of the ribs may extend substantially perpendicular to the aperture of the device. Some ribs may extend substantially perpendicular to the aperture that have a greater width than the width of any other ribs. The ribs may have a greater width and thickness as they extend radially away from the aperture. The ribs may continuously increase in width and thickness as they extend radially away from the aperture. One or more of the ribs may have a greater thickness than the thickness of one or more of the other ribs, as described above. The body may be hollow, and the ribs may be disposed on a surface internal to the tubular body. Ribs may be arranged just the top surface, on just the bottom surface or both the top and bottom surfaces. The ribs may be arranged symmetrically in a circular pattern around the aperture in a plane that is transverse to the longitudinal axis of the device, as described above. Ribs may be combined with other reinforcing features described herein, such as, for example, a ridge.

Figure 22A:
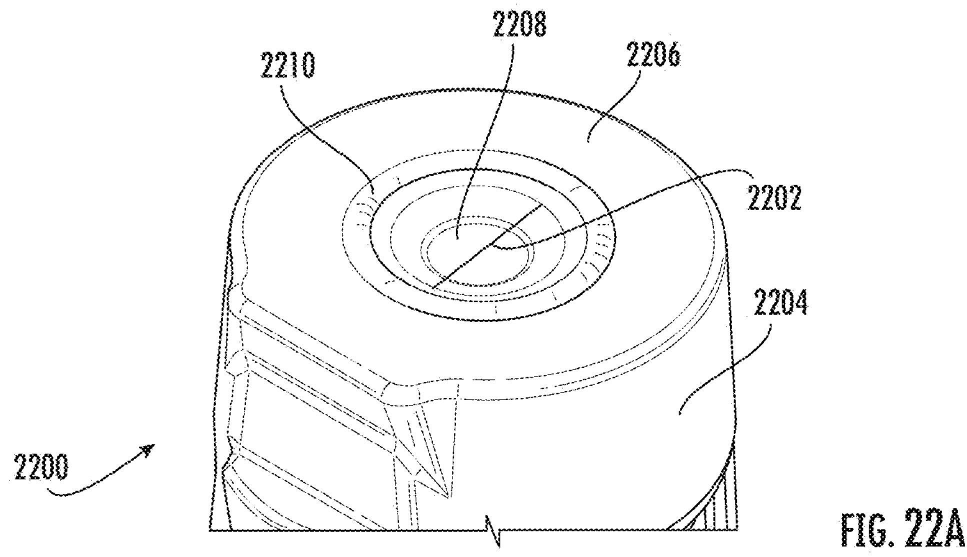
FIG. 22A illustrates an isometric view of a biopsy cap including a ridge, according to an embodiment of the present disclosure.
Figure 22B:
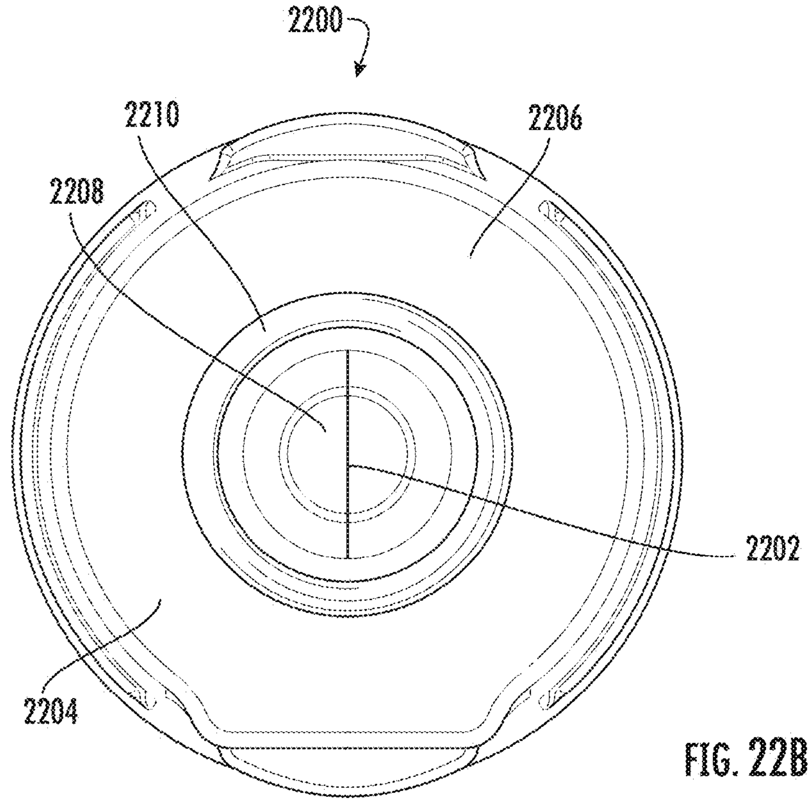
FIG. 22B illustrates a top view of the biopsy cap of FIG. 22A.

With reference to FIGS. 22A and 22B, an embodiment of a device for providing reinforced sealable access to a working channel is illustrated, which includes a biopsy cap 2200 with a tubular body 2204 having a closed substantially linear aperture 2202 at a proximal end 206 of the body 2204 configured to allow one or more medical instruments to be passed therethrough and, at the same time, substantially seal against fluids from the working channel passing therethrough. The distal end of the body 2204 (opposing the proximal end 2206) is configured to be installed in-line with the working channel at a proximal end or inlet port of the working channel. A ridge 2210 is disposed on the proximal end 2206 of the body 2204 that extends about the aperture 2202. The ridge 2210 has a perimeter outline about the aperture 2202 that is circular in shape, but may be any shape, e.g., ellipsoidal, oval, a combination of shapes, etc., to encompass the aperture 2202. The ridge 2210 has a cross-sectional thickness in a plane parallel to a longitudinal axis of the device 2200 that is thicker than an inner portion 2208 centrally within the ridge 2210 of the tubular body 2204. The thickness of a ridge 2210 may be a variety of thicknesses, e.g., the thickness of a ridge 2210 may be at least 25% more than a thickness of a wall of the proximal end 2206 of the body 2204 that the aperture 2202 extends through. For example, a ridge 2210 may have a peak thickness of about 0.071 inches (about 1.80 millimeters) and a thickness of a wall of the proximal end 2206 of the biopsy cap 2200 that the aperture 2202 extends through may be about 0.038 inches (about 0.97 millimeters). The thickness of the ridge 2210 provides resistance against a force from a medical instrument against the walls of the aperture 2202 that may otherwise tear the aperture 2202. A cross-section of the ridge 2210 is substantially semi-circular or half-moon in shape, however a multitude of other shapes may be employed, e.g., parabolic, curved, rectangular, tapered, a combination thereof, etc. The aperture 2202 does not extend to the ridge 2210, allowing for a minimal amount of tearing before the torn aperture 2202 propagates to the ridge 2210. The spacing between the ends of the aperture 2202 and the ridge 2210 may allow for a medical device that is almost as large or larger than the aperture 2202 to be inserted and passed through the aperture 2202 without undesirable resistance. Additionally, spacing between the ends of the aperture 2202 and the ridge 2210 may assist in preventing propagation of a tear in the aperture 2202.

With reference to FIGS. 23A and 23B, an embodiment of a device for providing reinforced sealable access to a working channel is illustrated, which includes a biopsy cap 2300 with a tubular body having a longitudinal axis and an aperture 2302 at a proximal end 2306 of the body. The biopsy cap 2300 is configured to be installed in-line with the working channel. The aperture 2302 is configured to allow one or more medical instruments to be passed therethrough and, at the same time, substantially seal against fluids from the working channel passing therethrough. The aperture 2302 has a reinforced pattern that extends in a plane substantially transverse to the longitudinal axis in more than one dimension. The aperture 2302 has a first end 2310, a second end 2312, and a third end 2314. The aperture 2302 extends substantially linearly from the first end 2312 to a split point 2316 and continues to extend from the split point 2316 separately and substantially linearly to each of the second and third ends 2312, 2314. This aperture 2302 allows for multiple medical instruments to be accepted and fixed into an end 2310, 312, 2314 of the aperture 2302, without multiple instruments occupying the same end 2310, 2312, 2314, which may reduce tearing of the aperture 2302 as will be discussed below with reference to FIGS. 24 and 25 and above with reference to FIGS. 18-20B. Although the portions of the aperture 2302 extending from the split point 2316 to each of the second and third ends 2312, 2314 are substantially the same length and extend at substantially the same angle degree from the split point 2316 to the first end and from an axis r of the aperture 2302, these angles and lengths may be variable, or some combination of uniform and variable among the ends. The angles may be such that the portions of the aperture 2302 extending from the split point 2316 to each of the second and third ends 2312, 2314 are oriented toward a locking channel configured to fix a medical device within the aperture 2302. Additionally, although three ends 2310, 2312, and 2314 are illustrated, any number of ends may be employed, e.g., a number of ends equivalent to a number of medical instruments to fix into a position. Although the portions of the aperture 2302 extending from the split point 2316 to the second and third ends 2312, 2314 are longer than the portion of the aperture 2302 extending from the first end 2310 to the split point 2316, these portions may be variable in length relative to each other or may be substantially equivalent. The second and third ends 2312, 2314 may be configured to each accommodate a single guidewire with substantially no tearing. An exemplary diameter of a guidewire may range from about 0.025 inches (about 0.635 millimeters) to about 0.038 inches (about 0.965 millimeters), and an exemplary length of the aperture 2302 from the first end 2310, along the axis r, to the split point 2316 may be about 0.040 inches (1.016 millimeters) while a greater length may be used to accommodate multiple guidewires, multiple instruments, and/or larger instruments through the aperture 2302. An exemplary length of the aperture 2302 from the split point 2316, to the second end 2312 or to the third end 2314 may be about 0.040 inches (1.016 millimeters) and may be less than about 0.050 inches (1.27 millimeters). A length of the aperture 2302 from the first end 2310, along the axis r, to a point between the second end 2312 and the third end 2314 may be about 0.080 inches (2.032 millimeters) to about 0.140 inches (3.556 millimeters). Although a ridge 2318 is illustrated about the aperture 2302 that is similar to the ridge 2210 discussed with respect to FIGS. 22A and 22B, various embodiments may include or exclude the ridge 2318.

With reference to FIG. 24, a top view of a biopsy cap 2400 is illustrated, which includes a substantially linear aperture 2402 extending from a first end 2404 to a second end 2406. Two medical instruments 2420 (e.g., guidewires) extend through the aperture 2402 at the second end 2406 and are forced against the walls of the aperture 2402 in the general direction of the vectors 2422 (e.g., during and after fixing the medical instruments 2420 into locking channels). The substantially linear aperture 2402 is opened at a first portion 2410 near the first end 2404 and is torn open at a second portion 2412 near the second end. This tearing and opening in FIG. 24 have opened the aperture 2402 to a larger gap space than any gap space that is illustrated in FIG. 19, which is a substantially linear tear that extends along the aperture 1902 of FIG. 19. The aperture 2402 is torn similarly to what is described with reference to the similar biopsy cap 2000 in FIGS. 20A and 20B above.

With reference to FIG. 25, a top view of an embodiment of a device for providing reinforced sealable access to a working channel is illustrated, which includes a biopsy cap 2500 with an aperture 2502 that has a reinforced pattern that extends in a plane substantially transverse to the longitudinal axis of the device in more than one dimension. Similar to the illustration and discussion of FIGS. 23A and 23B above, the aperture 2502 extends from a first end 2504 to a split point and thereafter extends to each of a second end 2506 and a third end 2508. Two medical instruments 2520 (e.g., guidewires) extend through the aperture 2502, one at each of the second end 2506 and the third end 2508. The medical instruments 2520 are forced against the walls of the aperture 2502 in the general direction of the vectors 2522 (e.g., during and after fixing the medical instruments 2520 into locking channels).

Comparing the force vectors 2422, 2522 and tearing in FIGS. 24 and 25, tearing has opened the apertures 2402, 2502 to more than what is illustrated in FIG. 19, which is substantially a linear tear that extends along the aperture 1902 of FIG. 19. The substantially linear apertures 2402, 2502 of FIGS. 24 and 25 are torn and/or opened at both a first portion 2410, 2510 near the first ends 2404, 2504 and at a second portion 2412, 2512 near the opposing ends (second ends 2406, 2506 and third end 2508). Because the reinforced pattern aperture 2502 of FIG. 25, according to an embodiment of the present disclosure, includes a separate second and third end 2506, 2508 for each of the medical devices 2520, the aperture 2502 may tear substantially linearly along the directions of the second end 2506 and third end 2508, resulting in open areas of the first portion 2510 and second portion 2512 of FIG. 25, which are smaller than the open areas of the first portion 2410 and second portion 2412 of FIG. 24 respectively, where there is not a reinforced pattern to the aperture. These smaller open areas of the portions 2510, 2512 of FIG. 25 when compared to the open areas of the portions 2410, 2412 of FIG. 24, allow for a better seal against the exchange of fluids across the aperture 2502 when instruments are passed therethrough.

Figure 26:
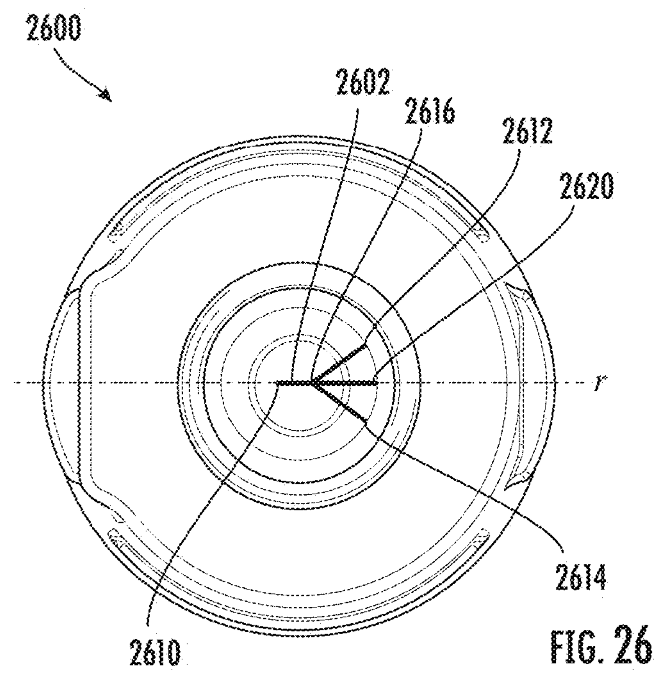
FIG. 26 illustrates a top view of a biopsy cap including an aperture extending in more than one dimension, according to an embodiment of the present disclosure.

FIG. 26 illustrates a top view of a biopsy cap 2600 including an aperture 2602 extending in more than one dimension, according to an embodiment of the present disclosure. The embodiment of FIG. 26 is the same as that of FIGS. 23A and 23B having an aperture 2602 that also includes a fourth end 2620. The fourth end 2620 extends opposite the first end 2610 and extends from the split point 2616 and substantially along the axis r, and is between the second and third ends 2612, 2614. The fourth end 2620 may accommodate an additional guidewire and/or may assist with passability of a medical device.

Figure 27A:
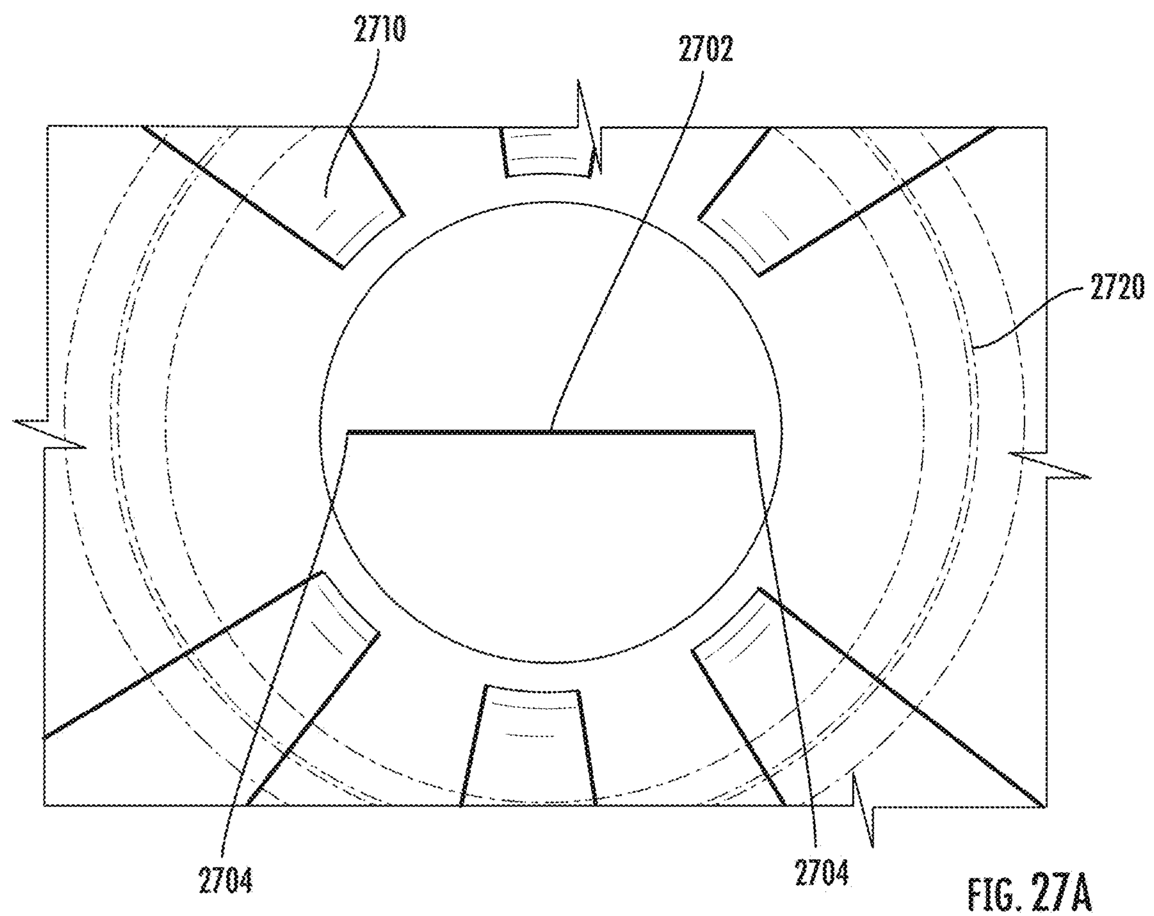
FIG. 27A illustrates a magnified view of a working channel side of an aperture of a biopsy cap, according to an embodiment of the present disclosure.
Figure 27B:
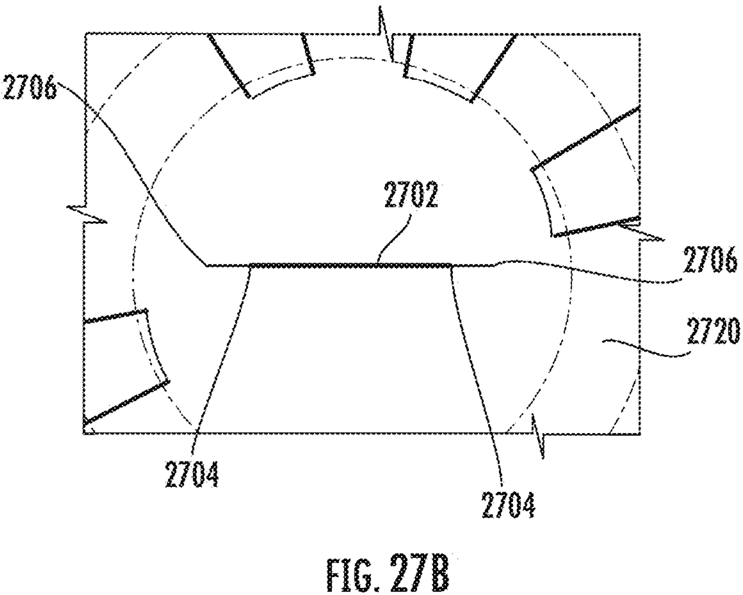
FIG. 27B illustrates a magnified view of a working channel side of an aperture of a used biopsy cap, according to an embodiment of the present disclosure.
Figure 27C:
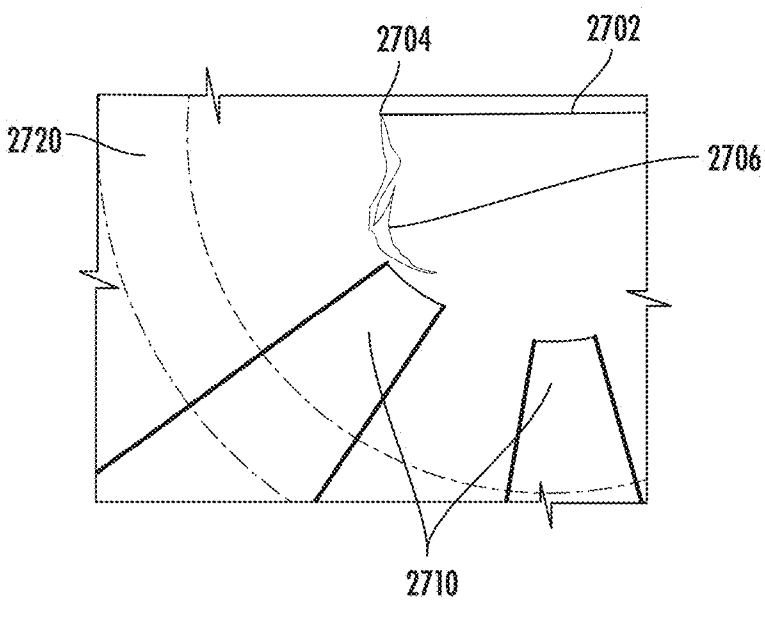
FIG. 27C illustrates a magnified view of a working channel side of an aperture of a used biopsy cap, according to an embodiment of the present disclosure.

FIGS. 27A-27C illustrate magnified views of biopsy caps, according to embodiments of the present disclosure. An aperture 2702 of the biopsy cap extends substantially linearly across a portion of the biopsy cap. The aperture 2702 has a length between the ends 2704 of the aperture 2702. During use of a biopsy cap, one or more medical instruments may be inserted through the aperture 2702, which may cause tearing. Tearing may be limited or tearing propagation may be reduced by the ribs 2710 and/or the ridge 2720 as described herein. With reference to FIG. 27A, the aperture 2702 of a biopsy cap including ribs 2710 and a ridge 2720 has not experienced any tearing after use. With reference to FIG. 27B, the original length of the aperture 2702 between the ends 2704 has been torn to a larger-sized aperture between the torn ends 2706, but the tearing has not propagated in a manner so-as to affect the functionality of the biopsy cap. The original aperture 2702 length of FIG. 27B (between the ends 2704) may be about 1.5 mm to about 4 mm, while the torn aperture 2702 length (between the torn ends 2706) may be at least about 5 mm. With reference to FIG. 27C, an aperture 2702 may tear toward a torn end 2706 having a tear path that is substantially non-linear with the aperture 2702 (i.e., along a line between the original ends 1004). The non-linear tear end 2706 is maintained radially within the ridge 2720 and also radially within the ribs 2710.

Referring to FIGS. 28A-28D, a base 2830 according to an embodiment of the present disclosure is illustrated, which includes a recessed annular portion 2832. It will be appreciated that the recessed annular portion 2832 may be complementary to a securing member 140 formed as part of a biopsy cap 130, 2900 (e.g., FIG. 3 above and FIG. 29 below), and thus the biopsy cap 130 may be secured to the base 2830 via a frictional fit. The base 2830 and/or a biopsy cap may be formed of a sufficiently flexible material in order to enable the biopsy cap to be snap-fit into position on the base 2830. The base 2830 also defines a securement region 2840 that may be configured to frictionally engage a port 20 (e.g., FIG. 2). Extensions 2844 extend distally from the base 2830 on either side of the securement region 2840. The extensions 2844 may assist a user with orienting the securement region 2840 onto the port 20 such that at least one of the extensions 2844 comes into contact and may engage with a mating surface of the port 20. The extensions 2844 may also assist the user as a handle for the user to remove the base 2830 from the port 20. An aperture 2842 extends through the base 2830 in order to accommodate an elongate member extending through the biopsy cap 130, 2900 and base 2830. The proximal end 2834 of the base 2830 forming the aperture 2842 has a funnel-like shape that may funnel fluids and/or instruments distally into the aperture 2842. The sloping funnel-like shape of the proximal end 2834 has a a slope at a first angle $\alpha$ that transitions distally to a second angle $\beta$. Angle $\alpha$ may be smaller than Angle $\beta$ such that the proximal end 2834 transitions (i.e., tapers) from a thicker angle $\alpha$ portion to a thinner angle $\beta$ portion toward the aperture 2842, allowing for greater passability (i.e., less axial force to translate instrument) closer to the aperture 2842 than away from the aperture 2842. The $\alpha$ and $\beta$ angles may be any angle between 0-360 degrees, e.g., angle $\alpha$ may be about 30° and angle $\beta$ may be about 45°. The securement region 2840 installed about the port 20 may act as a primary seal, while a ridge 2846 extending about the securement region 2840 that compressively engages a top surface of the port 20 may act as a secondary seal.

Figure 29:
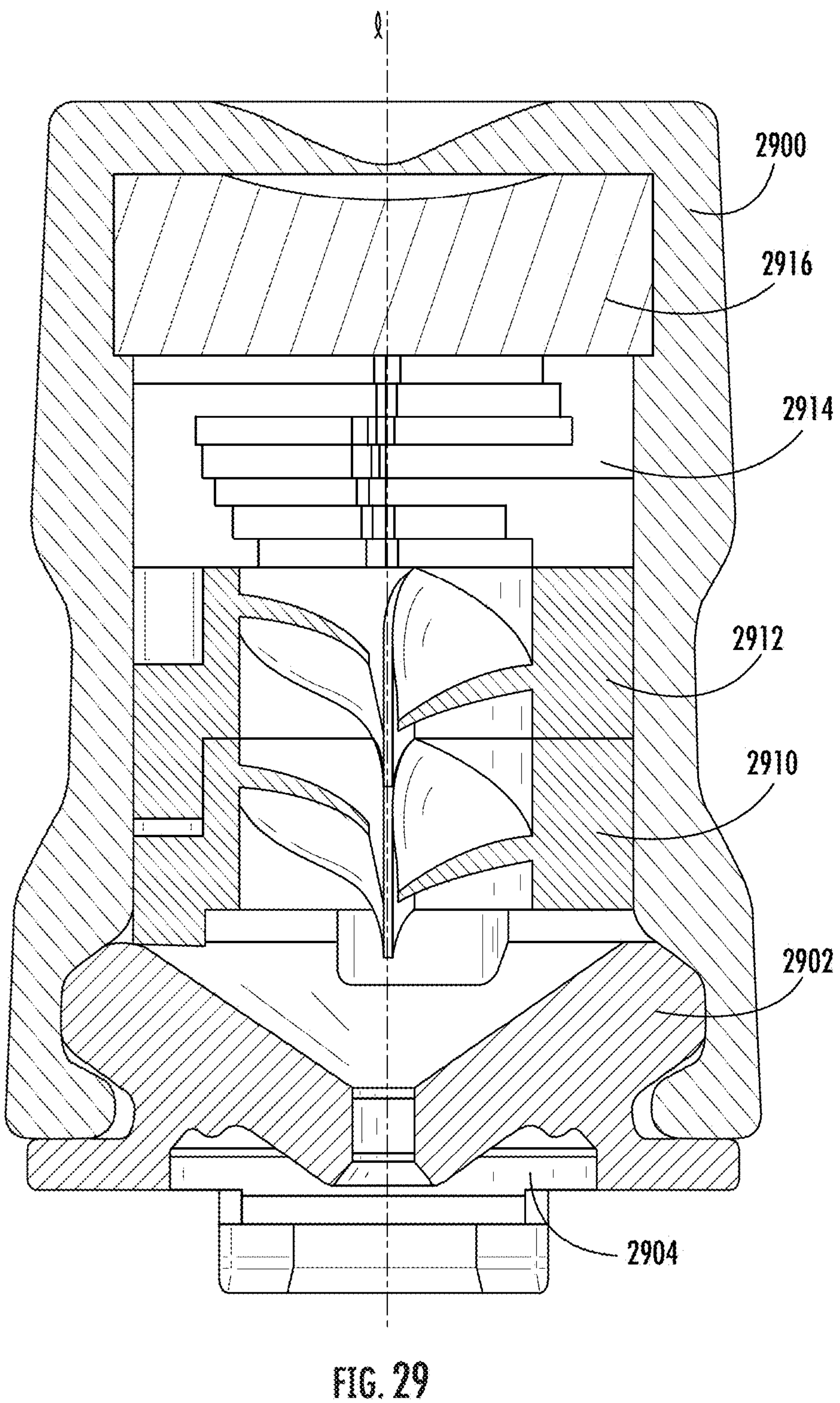
FIG. 29 illustrates a cross-sectional view of an assembly of a biopsy cap, including sealing members and a base, according to an embodiment of the present disclosure.

FIG. 29 illustrates a cross-sectional view of an assembly of a biopsy cap 2900, a base 2902, and sealing members 2910, 2912, 2914, 2916, according to an embodiment of the present disclosure. The sealing members 2910, 2912, 2914, 2916 are disposed within the biopsy cap 2900 and the cap 2900 onto the base 2902. The entire assembly may be coupled to a port by securing a securement region 2904 to the port such that the apertures of the biopsy cap 2900, base 2902, sealing members 2910, 2912, 2914, 2916, and port are all substantially aligned axially along a longitudinal axis C. Any sealing member discussed throughout this disclosure are suitable for assembly in the biopsy cap 2900.

In various embodiments, an aperture of a biopsy cap may not extend entirely through a wall of the biopsy cap. An aperture may terminate at a certain distance within a thickness of a wall of a biopsy cap, so that the remaining thickness of the wall at the aperture may be punctured through by a medical instrument in use. Alternatively, an aperture may be covered by a membrane that may be adhered to the wall of a biopsy cap such that it is disposed across the aperture before it is punctured by a medical instrument in use.

In various embodiments, a length or portions of a length of an aperture may range from about 2 mm to about 5 mm, about 1.5 mm to about 4 mm, about 3 mm, etc. A length of a portion having an end of a "Y-shaped" aperture may be about 3 mm. The length of a tear propagating from an aperture may compromise the functionality of a biopsy cap depending on the length of the aperture. For example, a medical instrument causing a tear having a length of about 10% of the length of an aperture may be significant enough to affect the performance of the biopsy cap.

In various embodiments, a biopsy cap may comprise flexible materials such as silicone, liquid silicone rubber, rubber, polymer, elastomer, thermoplastic elastomer (TPE), flexible plastic, or combinations thereof. Variable thicknesses across the cap may be employed for various functions, e.g., a thicker body for installing securely in-line with a working channel, a thinner wall about an aperture for passage of medical devices, a thicker ridge about an aperture to prevent extended tearing, thicker rib portions to assist in maintaining a closed position of an aperture, or the like.

In various embodiments, a biopsy cap may be molded into a tubular body to make up a formation or shape that is configured or customized to be installed into a particular housing and/or be compatible with a particular working channel. A patterned aperture according to the embodiments described here or otherwise according to the present disclosure may be cut into the formation.

The various biopsy caps, seal members, and molds as well as the various components thereof may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In addition, portions or components of the structures (including the various securing members, locking members, etc.) disclosed herein may be coated with a relatively soft material that may improve grip such as a thermoplastic elastomer. The coating may or may not include additional features that may improve grip such as ridges, surface textures, bumps, grooves, projections, etc.

Furthermore, the various structures disclosed herein may be designed for single use or may be designed for repeated uses. Thus, the structures disclosed herein may be manufactured from materials that can withstand multiple sterilizations and/or cleanings. This may be true of entire caps, as disclosed herein, or any of the various features of any of the caps.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A seal assembly, comprising:

a biopsy cap having a first end and a second end, an inner chamber defined therein between the first end and the second end, and a cap aperture at the first end in fluid communication with the inner chamber;

a plurality of seal members disposed within the inner chamber, each seal member of the plurality of seal members having a seal aperture in fluid communication with the cap aperture; and a base frictionally secured to the inner chamber, the base having a base aperture therethrough in fluid communication with each of the seal apertures, a securement region configured to engage a port of an endoscope, and an extension extending distally beyond the securement region;

wherein:

the plurality of seal members are disposed between the base and the first end of the biopsy cap;

the biopsy cap and the base are configured to be frictionally secured together; and the extension extends along a limited extent around the circumference of the base and is configured to assist the user as a handle for the user to remove the base from the port.

2. The assembly of claim 1, wherein the base further comprises a recess configured to engage the biopsy cap frictionally.

3. The assembly of claim 2, wherein the recess is an external annular recess.

4. The assembly of claim 1, wherein a proximal end of the base has a slope towards the base aperture, the slope having a first angle that transitions to a second angle, wherein the second angle is between the first angle and the aperture, and wherein the second angle is larger than the first angle.

5. The assembly of claim 4, wherein the first angle is about 30° and the second angle is about 45°.

6. The assembly of claim 1, wherein the base further comprises at least two extensions that extend distally from the base and are configured to engage a port of an endoscope.

7. The assembly of claim 1, wherein each of the apertures of the plurality of seal members are axially aligned with each other, the base aperture, and the cap aperture.

8. The assembly of claim 1, wherein at least one of the plurality of seal members comprises a plurality of surfaces extending radially about the seal aperture in a helical pattern.

9. The assembly of claim 1, wherein at least one of the plurality of seal members comprises a plurality of projections extending radially inward towards the seal aperture, wherein the plurality of projections are angularly offset layers.

10. The assembly of claim 9, wherein the plurality of projections define the seal aperture at the center of the seal member such that the seal aperture extends axially through the seal member.

11. A device configured to attach to a port of an endoscope, the device comprising:

a biopsy cap; and a base defining an aperture therethrough in fluid communication with a port of an endoscope, and having a securement region configured to engage the port and an extension extending distally beyond the securement region and circumferentially along a limited extent of the circumference of the base;

wherein:

the base engages the top surface of the port;

the base is configured to engage the distal end of the biopsy cap to retain the base frictionally with respect to the biopsy cap; and the extension is configured to assist the user as a handle for the user to remove the base from the port.

12. The device of claim 11, wherein the base further comprises a recess and the recess is an external annular recess.

13. The device of claim 11, wherein a proximal end of the base has a slope towards the aperture, the slope having a first angle that transitions to a second angle, wherein the second angle is between the first angle and the aperture, and wherein the second angle is larger than the first angle.

14. The device of claim 11, wherein at least one of the base or the biopsy cap is formed of a material enabling the base to be snap-fit into position with respect to the biopsy cap.

15. The device of claim 11, wherein the base includes the extension and at least one additional extension extending distally out of the base to engage the port of the endoscope.

16. The device of claim 11, further comprising a ridge about the aperture configured to compressively seal against the port.

17. A seal system, comprising:

an endoscope having a working channel and a port at a proximal end of the working channel;

a base having a base aperture therethrough, a securement region configured to engage the port, and an extension extending distally beyond the securement region and circumferentially along a limited extent of the circumference of the base; and a biopsy cap having a first end with a cap aperture therethrough in fluid communication with the base aperture and the port, a second end, and an inner chamber defined therein between the first end and the second end and in which the base is disposed;

wherein:

the base is frictionally secured to the second end of the biopsy cap to be secured thereto, and the extension extends distally from the base and beyond the securement region and the second end of the biopsy cap, and is configured to assist the user as a handle for the user to remove the base from the port.

18. The system of claim 17, further comprising a medical instrument extending through the cap aperture, the base aperture, and the port.

19. The system of claim 17, further comprising a seal member disposed within an inner chamber of the biopsy cap and between the base and the first end of the biopsy cap, the seal member having a seal aperture in fluid communication with the cap aperture.

20. The system of claim 17, wherein the base further comprises an external recess configured to engage the biopsy cap frictionally.

* * * * *